(12) United States Patent
Lindquist et al.

(10) Patent No.: US 9,249,444 B2
(45) Date of Patent: Feb. 2, 2016

(54) MODULATORS OF ALPHA-SYNUCLEIN TOXICITY

(71) Applicant: Whitehead Institute for Biomedical Research, Cambridge, MA (US)

(72) Inventors: Susan L. Lindquist, Cambridge, MA (US); Aaron D. Gitler, Philadelphia, PA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 13/931,004

(22) Filed: Jun. 28, 2013

(65) Prior Publication Data

US 2014/0051091 A1 Feb. 20, 2014

Related U.S. Application Data

(63) Continuation of application No. 12/809,859, filed as application No. PCT/US2008/088022 on Dec. 22, 2008, now Pat. No. 8,501,465.

(60) Provisional application No. 61/090,797, filed on Aug. 21, 2008, provisional application No. 61/016,214, filed on Dec. 21, 2007.

(51) Int. Cl.
| | | |
|---|---|---|
| *C07H 21/02* | (2006.01) | |
| *C07H 21/04* | (2006.01) | |
| *C12N 15/85* | (2006.01) | |
| *C12Q 1/02* | (2006.01) | |
| *C12Q 1/68* | (2006.01) | |
| *G01N 33/68* | (2006.01) | |

(52) U.S. Cl.
CPC .............. *C12Q 1/025* (2013.01); *C12Q 1/6883* (2013.01); *G01N 33/68* (2013.01); *C12Q 2600/136* (2013.01); *C12Q 2600/158* (2013.01); *G01N 2500/10* (2013.01)

(58) Field of Classification Search
CPC .................................................... C12N 15/113
See application file for complete search history.

(56) References Cited

U.S. PATENT DOCUMENTS

| | | | |
|---|---|---|---|
| 6,541,195 B2 | 4/2003 | Welch et al. | |
| 7,045,290 B2 | 5/2006 | Lindquist et al. | |
| 7,452,670 B2 | 11/2008 | Muchowski et al. | |
| 7,799,535 B1 | 9/2010 | Lindquist | |
| 2002/0137086 A1 | 9/2002 | Olek et al. | |
| 2003/0022243 A1 | 1/2003 | Kondejewski et al. | |
| 2003/0073610 A1 | 4/2003 | Lindquist et al. | |
| 2003/0148264 A1 | 8/2003 | Held et al. | |
| 2003/0170678 A1 | 9/2003 | Tanzi et al. | |
| 2003/0171255 A1 | 9/2003 | Greengard et al. | |
| 2003/0211989 A1 | 11/2003 | Plowman et al. | |
| 2004/0101874 A1 | 5/2004 | Ghosh et al. | |
| 2005/0064548 A1 | 3/2005 | Lindquist et al. | |
| 2006/0084071 A1* | 4/2006 | Muchowski ..................... 435/6 |
| 2007/0092889 A1 | 4/2007 | Cox et al. | |
| 2008/0045607 A1 | 2/2008 | Lindquist et al. | |
| 2008/0249129 A1 | 10/2008 | Lindquist et al. | |
| 2009/0099069 A1 | 4/2009 | Lindquist et al. | |
| 2009/0304664 A1 | 12/2009 | Lindquist et al. | |
| 2010/0279943 A1 | 11/2010 | Zisapel et al. | |

FOREIGN PATENT DOCUMENTS

| | | |
|---|---|---|
| EP | 1 736 154 | 12/2006 |
| WO | WO2004093790 | 11/2004 |
| WO | WO2005067391 | 7/2005 |
| WO | WO2006065555 | 6/2006 |

OTHER PUBLICATIONS

Agami, R., "RNAi and related mechanisms and their potential use for therapy," Chem. Biol. (2002), 6(6):829-34.

Berkey, C.D. et al., "Nrg1 and Nrg2 Transcriptional Repressors Are Differently Regulated in Response to Carbon Source," Eukaryot Cell (2004), 3(2):311-317.

Cooper, A. et al., "α-synuclein blocks ER-Golgi traffic and Rab1 rescues neuron loss in Parkinson's models," Science (2006), 313(5785):324-328.

De Antoni, A. et al., "Significance of GTP Hydrolysis in Yptlp-regulated Endoplasmic Reticulum to Golgi Transport Revealed by the Analysis of Two Novel Yptl-GAPs," Journal of Biological Chemistry ( 2002), 277(43):41023-41031.

De Mesquita et al., "*In silico* and in vivo analysis reveal a novel gene in *Sacchceromyces cerevisiae* trehalose methobolism," BMC Genomics (2003), 4(1):45-40.

Di Fonzo et al., ATP13A2 missense mutations in juvenile parkinsonism and young onset Parkinson disease. Neurology 2007;68: 1557-62.

Fleming, T. et al., "Yeast Cells Provide Insight into Alpha-Synuclein Biology and Pathobiology," Science 2003), 302(5651):1772-1775.

Gitler et al., Alpha-synuclein is part of a diverse and highly conserved interaction network that includes PARK9 and manganese toxicity. Nat Genet. 2009;41(3):308-15.

Kaniak, A. et al. "Regulatory Network Connecting Two Glucose Signal Transduction Pathways in *Saccharomyces cerevisiae*," Eukaryotic Cell (2004), 3(1):221-231.

Kawamata, H., et al., "Interaction of α-synuclein and synphilin-1: effect of Parkinson's disease-associated mutations," J. Neurochem. (2001) 77(3):929-34.

(Continued)

*Primary Examiner* — Amy Bowman
(74) *Attorney, Agent, or Firm* — Fish & Richardson P.C.

(57) ABSTRACT

Disclosed are genes that, when overexpressed in cells expressing alpha-synuclein, either suppress or enhance alpha-synuclein mediated cellular toxicity. Compounds that modulate expression of these genes or activity of the encoded proteins can be used to inhibit alpha-synuclein mediated toxicity and used to treat or prevent synucleinopathies such as Parkinson's disease. Also disclosed are methods of identifying inhibitors of alpha-synuclein mediated toxicity.

8 Claims, No Drawings

(56) References Cited

OTHER PUBLICATIONS

Kirk, N. et al., "Growth rate influences MF alpha 1 promoter activity in MAT alpha *Saccaharomyces cerevisiae*," Appl. Microbiol. Biotechnol. (1994), 42(2):340-345. Abstract only.

Lees et al., Clinical heterogeneity of ATP13A2 linked disease (Kufor-Rakeb) justifies a PARK designation. Neurology 2007;68: 1553-54.

Neystat, M., et al., "Analysis of synphilin-1 and synuclein interactions by yeast two-hybrid β-galactosidase liquid assay," Neuroscience Letters (2002) 325(2):119-23.

Peng, X. M. et al., "α-Synuclein activation of protein phosphatase 2A reduces tyrosine hydroxylase phosphorylation in dopaminergic cells," Journal of Cell Sciences (2005), 118(15:3523-3530.

Ramirez et al., Hereditary parkinsonism with dementia is caused by mutations in ATP13A2, encoding a lysosomal type 5 P-type ATPase. Nat Genet 2006;38: 1184-91.

Song, L. et al., "Central Role of Glycogen Synthase Kinase-3β in Endoplasmic Reticulum Stress-induced induced Caspase-3 Activation," (2002), 277(47):44701-44708.

Takahashi, R., "Neurodegeneration caused by ER stress?—The pathogenetic mechanisms underlying AR-JP," Folia Pharmacologica Japonica, (2004), 124(6):375-382.

Takahashi, R., "Pael receptor/GPR 37 and Parkinson's disease," Journal of Clinical and Experimental Medicine, (2005), 212(1):66-70.

Takahashi, R., Seikagaku, Biochemistry (2002), 74(6):471-476 (with partial translation).

Willingham, S. et al., "Yeast Genes that Enhance the Toxicity of a Mutant Huntingtin Fragment of α-Synuclein," Science (2003), 302(5651):1769-1772.

* cited by examiner

MODULATORS OF ALPHA-SYNUCLEIN TOXICITY

CROSS REFERENCE TO RELATED APPLICATIONS

This application is a continuation of U.S. application Ser. No. 12/809,859, filed Sep. 20, 2010, which is a U.S. national stage of PCT Application No. PCT/US2008/088022, filed Dec. 22, 2008, which claims priority from U.S. Provisional Application No. 61/016,214, filed Dec. 21, 2007, and U.S. Provisional Application No. 61/090,797, filed Aug. 21, 2008. The entire content of each of these prior applications is incorporated herein by reference in its entirety.

STATEMENT AS TO FEDERALLY SPONSORED RESEARCH

This invention was made with Government support under grant number 2P50 NS038372-0681 awarded by the National Institutes of Health. The Government has certain rights in the invention.

TECHNICAL FIELD

This invention relates to compositions and methods for inhibiting alpha-synuclein mediated toxicity and methods for identifying inhibitors of alpha-synuclein mediated toxicity.

BACKGROUND

Parkinson's disease is a neurodegenerative disorder that is pathologically characterized by the presence of intracytoplasmic Lewy bodies (Lewy in Handbuch der Neurologie, M. Lewandowski, ed., Springer, Berlin, pp. 920-933, 1912; Pollanen et al., J. Neuropath. Exp. Neurol. 52:183-191, 1993), the major components of which are filaments consisting of alpha-synuclein (Spillantini et al., Proc. Natl. Acad. Sci. USA 95:6469-6473, 1998; Arai et al., Neurosci. Lett. 259:83-86, 1999), a 140-amino acid protein (Ueda et al., Proc. Natl. Acad. Sci. USA 90:11282-11286, 1993). Two dominant mutations in alpha-synuclein causing familial early onset Parkinson's disease have been described, suggesting that Lewy bodies contribute mechanistically to the degeneration of neurons in Parkinson's disease and related disorders (Polymeropoulos et al., Science 276:2045-2047, 1997; Kruger et al., Nature Genet. 18:106-108, 1998; Zarranz et al., Ann. Neurol. 55:164-173, 2004). Triplication and duplication mutation of the alpha-synuclein gene have been linked to early-onset of Parkinson's disease (Singleton et al., Science 302:841, 2003; Chartier-Harlin at al. Lancet 364:1167-1169, 2004; Ibanez et al., Lancet 364:1169-1171, 2004). In vitro studies have demonstrated that recombinant alpha-synuclein can indeed form Lewy body-like fibrils (Conway et al., Nature Med. 4:1318-1320, 1998; Hashimoto et al., Brain Res. 799:301-306, 1998; Nahri et al., J. Biol. Chem. 274:9843-9846, 1999). Both Parkinson's disease-linked alpha-synuclein mutations accelerate this aggregation process, demonstrating that such in vitro studies may have relevance for Parkinson's disease pathogenesis. Alpha-synuclein aggregation and fibril formation fulfills the criteria of a nucleation-dependent polymerization process (Wood et al., J. Biol. Chem. 274:19509-19512, 1999). In this regard alpha-synuclein fibril formation resembles that of Alzheimer's β-amyloid protein (Aβ) fibrils. Alpha-synuclein recombinant protein, and non-Aβ component (known as NAC), which is a 35-amino acid peptide fragment of alpha-synuclein, both have the ability to form fibrils when incubated at 37° C., and are positive with amyloid stains such as Congo red (demonstrating a red/green birefringence when viewed under polarized light) and Thioflavin S (demonstrating positive fluorescence) (Hashimoto et al., Brain Res. 799:301-306, 1998; Ueda et al., Proc. Natl. Acad. Sci. USA 90:11282-11286, 1993).

Synucleins are a family of small, presynaptic neuronal proteins composed of α-, β-, and γ-synucleins, of which only alpha-synuclein aggregates have been associated with several neurological diseases (Ian et al., Clinical Neurosc. Res. 1:445-455, 2001; Trojanowski and Lee, Neurotoxicology 23:457-460, 2002). The role of synucleins (and in particular, alpha-synuclein) in the etiology of a number of neurodegenerative and/or amyloid diseases has developed from several observations. Pathologically, alpha-synuclein was identified as a major component of Lewy bodies, the hallmark inclusions of Parkinson's disease, and a fragment thereof was isolated from amyloid plaques of a different neurological disease, Alzheimer's disease. Biochemically, recombinant alpha-synuclein was shown to form amyloid-like fibrils that recapitulated the ultrastructural features of alpha-synuclein isolated from patients with dementia with Lewy bodies, Parkinson's disease and multiple system atrophy. Additionally, the identification of mutations within the alpha-synuclein gene, albeit in rare cases of familial Parkinson's disease, demonstrated an unequivocal link between synuclein pathology and neurodegenerative diseases. The common involvement of alpha-synuclein in a spectrum of diseases such as Parkinson's disease, dementia with Lewy bodies, multiple system atrophy and the Lewy body variant of Alzheimer's disease has led to the classification of these diseases under the umbrella term of "synucleinopathies."

Fibrillization and aggregation of alpha-synuclein is thought to play major role in neuronal dysfunction and death of dopaminergic neurons in Parkinson's disease. Mutations in alpha-synuclein or genomic triplication of wild type alpha-synuclein (leading to its overexpression) cause certain rare familial forms of Parkinson's disease. In vitro and in vivo models suggest that over-expression of wild-type alpha-synuclein induces neuronal cell death. See, e.g., Polymeropoulos, et al. (1997) Science 276(5321):2045-7, Kruger, et al. (1998) Nat. Genet. 18(2):106-8, Singleton, et al. (2003) Science 302(5646):841, Miller, et al. (2004) Neurology 62(10): 1835-8, Hashimoto, et al. (2003) Ann NY Acad. Sci. 991:171-88, Lo Bianco, et al. (2002) Proc Natl Acad Sci USA. 99(16): 10813-8, Lee, et al. (2002) Proc Natl Acad Sci USA. 99(13): 8968-73, Masliah, et al. (2000) Science 287(5456):1265-9, Auluck, et al. (2002) Science 295(5556):865-8, Oluwatosin-Chigbu et al. (2003) Biochem Biophys Res Commun 309(3): 679-84, Klucken et al. (2004) J Biol. Chem. 279(24):25497-502. Protecting neurons from the toxic effects of alpha-synuclein is a promising strategy for treating Parkinson's disease and other synucleinopathies such as Lewy body dementia.

Thus, there is a need for compounds and compositions that prevent alpha-synuclein toxicity and/or aggregation and/or promote alpha-synuclein fibril disaggregation. Such compounds and compositions are useful in treating or ameliorating one or more symptoms of alpha-synuclein mediated diseases and disorders, or diseases and disorders in which alpha-synuclein toxicity is implicated, including but not limited to, Parkinson's disease (including Parkinson's disease chemically induced by exposure to environmental agents such as pesticides, insecticides, or herbicides and/or metals such as manganese, aluminum, cadmium, copper, or zinc, SNCA gene-linked Parkinson's disease, sporadic or idiopathic Parkinson's disease, or Parkin- or LRRK2-linked Parkinson's disease), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam.

SUMMARY

The invention is based, at least in part, on the discovery that certain genes, when overexpressed in cells expressing alpha-synuclein, either suppress or enhance alpha-synuclein mediated cellular toxicity. The identification of these genes as relevant to alpha-synuclein mediated toxicity permits the carrying out of screens to identify compounds that modulate toxicity. Compounds identified by such screens can be used as candidate drugs for the treatment or prevention of synucleinopathies such as Parkinson's disease.

The disclosure features methods of inhibiting alpha synuclein-mediated cellular toxicity by contacting a cell expressing a toxicity-inducing amount or form of alpha synuclein with an effective amount of a compound that inhibits expression or activity of GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2.

Also disclosed are methods of inhibiting alpha synuclein-mediated cellular toxicity by contacting a cell expressing a toxicity-inducing amount or form of alpha synuclein with an effective amount of a compound that inhibits expression or activity of NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2.

In some embodiments, the compound used in the methods contains a nucleic acid that inhibits translation of an RNA encoding the protein. In other embodiments, the compound used in the methods contains a nucleic acid that inhibits transcription of a DNA encoding the protein.

Also disclosed are methods of identifying a compound that inhibits alpha synuclein-mediated toxicity by: (i) providing a cell expressing an amount or form of alpha synuclein that reduces viability of the cell; (ii) contacting the cell with an agent that inhibits expression or activity of GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; and (iii) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) providing a cell expressing an amount or form of alpha synuclein that reduces viability of the cell; (ii) contacting the cell with an agent that inhibits expression or activity of NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; and (iii) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) screening to identify an agent that inhibits expression or activity of GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; (ii) providing a cell expressing an amount or form of alpha synuclein that reduces viability of the cell; (iii) contacting the cell with the agent; and (iv) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) screening to identify an agent that inhibits expression or activity of NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; (ii) providing a cell expressing an amount or form of alpha synuclein that reduces viability of the cell; (iii) contacting the cell with the agent; and (iv) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits expression of a protein by: (i) providing a cell expressing GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; (ii) contacting the cell with an agent; and (iii) measuring the expression of the protein in the presence of the agent, wherein a reduction in the expression of the protein in the presence of the agent as compared to the expression of the protein in the absence of the agent identifies the agent as a compound that inhibits the expression of the protein.

Also disclosed are methods of identifying a compound that inhibits expression of a protein by: (i) providing a cell expressing NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2; (ii) contacting the cell with an agent; and (iii) measuring the expression of the protein in the presence of the agent, wherein a reduction in the expression of the protein in the presence of the agent as compared to the expression of the protein in the absence of the agent identifies the agent as a compound that inhibits the expression of the protein.

Also disclosed are methods of identifying a compound that inhibits expression of a protein by: (i) providing a cell containing a reporter construct containing (a) a promoter sequence of a gene encoding GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2, and (b) a nucleotide sequence encoding a reporter protein; (ii) contacting the cell with an agent; and (iii) measuring the expression of the reporter protein in the presence of the agent, wherein a reduction in the expression of the reporter protein in the presence of the agent as compared to the expression of the reporter protein in the absence of the agent identifies the agent as a compound that inhibits the expression of the protein.

Also disclosed are methods of identifying a compound that inhibits expression of a protein by: (i) providing a cell containing a reporter construct containing (a) a promoter sequence of a gene encoding NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2, and (b) a nucleotide sequence encoding a reporter protein; (ii) contacting the cell with an agent; and (iii) measuring the expression of the reporter protein in the presence of the agent, wherein a reduction in the expression of the reporter protein in the presence of the agent as compared to the expression of the reporter protein in the absence of the agent identifies the agent as a compound that inhibits the expression of the protein.

Also disclosed are methods of identifying a compound that inhibits the activity of a protein by: (i) providing a GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2 protein; (ii) contacting the protein with an agent; and (iii) measuring the activity of the protein in the presence of the agent, wherein a reduction in the activity of the protein in the presence of the agent as compared to the activity of the protein in the absence of the agent identifies the agent as a compound that inhibits the activity the protein.

Also disclosed are methods of identifying a compound that inhibits the activity of a protein by: (i) providing a NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2 protein; (ii) contacting the protein with an agent; and (iii) measuring the activity of the protein in the presence of the agent, wherein a reduction in the activity of the protein in the presence of the agent as compared to the activity of the protein in the absence of the agent identifies the agent as a compound that inhibits the activity the protein.

In the foregoing methods, the agent can be a synthetic compound or a naturally occurring compound. For example, the agent can be a small molecule, nucleic acid, protein, antibody, or peptidomimetic. The cell used in the methods can be a eukaryotic cell (e.g., a yeast cell, nematode cell, insect cell, or mammalian cell), a prokaryotic cell, or a cell obtained from an alpha-synuclein transgenic animal.

Also disclosed are methods of treating or preventing a synucleinopathy by administering to a subject in need thereof a pharmaceutical composition containing a therapeutic or prophylactic amount of a compound that decreases the expression or activity of GOSR1, SEC31A, SEC31B, ADIPOR2, ADIPOR1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, and/or USP2.

Also disclosed are methods of treating or preventing a synucleinopathy by administering to a subject in need thereof a pharmaceutical composition containing a therapeutic or prophylactic amount of a compound that decreases the expression or activity of KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, and/or USP2.

Also disclosed are methods of treating or preventing a synucleinopathy by administering to a subject in need thereof a pharmaceutical composition containing a therapeutic or prophylactic amount of a compound that enhances the expression or activity of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5.

In some embodiments of the foregoing methods, the synucleinopathy is Parkinson's disease (including Parkinson's disease chemically induced by exposure to environmental agents such as pesticides, insecticides, or herbicides and/or metals such as manganese, aluminum, cadmium, copper, or zinc, SNCA gene-linked Parkinson's disease, sporadic or idiopathic Parkinson's disease, or Parkin- or LRRK2-linked Parkinson's disease), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam. A compound that enhances the expression or activity of a protein includes, for example, a compound that inhibits the degradation of the protein.

In some embodiments of the foregoing methods, the pharmaceutical composition contains (i) a therapeutic or prophylactic amount of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5, and (ii) a pharmaceutically acceptable carrier.

Also disclosed are methods of inhibiting alpha synuclein-mediated cellular toxicity by contacting a cell expressing a toxicity-inducing amount or form of alpha synuclein with an effective amount of a compound that enhances expression or activity of QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5.

Also disclosed are methods of inhibiting alpha synuclein-mediated cellular toxicity by contacting a cell expressing a toxicity-inducing amount or form of alpha synuclein with an effective amount of a compound that enhances expression or activity of DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5.

Also disclosed are methods of identifying a compound that inhibits alpha synuclein-mediated toxicity by: (i) providing a cell expressing an amount or form of alpha synuclein that reduces viability of the cell; (ii) contacting the cell with an agent that enhances expression or activity of QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; and (iii) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) providing a cell expressing an amount or form of alpha synuclein that reduces viability of the cell; (ii) contacting the cell with an agent that enhances expression or activity of DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; and (iii) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) screening to identify an agent that enhances expression or activity of QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; (ii) providing a cell expressing an amount or form of alpha synuclein that reduces viability of the cell; (iii) contacting the cell with the agent; and (iv) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that inhibits alpha synuclein-mediated toxicity by: (i) screening to identify an agent that enhances expression or activity of DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; (ii) providing a cell expressing an amount or form of alpha synuclein that reduces viability of the cell; (iii) contacting the cell with the agent; and (iv) measuring cell viability in the presence of the agent, wherein an increase in cell viability in the presence of the agent as compared to cell viability in the absence of the agent identifies the agent as a compound that inhibits alpha synuclein-mediated toxicity.

Also disclosed are methods of identifying a compound that increases expression of a protein by: (i) providing a cell expressing a QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5 protein; (ii) contacting the cell with an agent; and (iii) measuring the expression of the protein in the presence of the agent, wherein an increase in the expression of the protein in the presence of the agent as compared to the expression of the protein in the absence of the agent identifies the agent as a compound that increases the expression of the protein.

Also disclosed are methods of identifying a compound that increases expression of a protein by: (i) providing a cell expressing a DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5 protein; (ii) contacting the cell with an agent; and (iii) measuring the expression of the protein in the presence of the agent, wherein an increase in the expression of the protein in the presence of the agent as compared to the expression of the protein in the absence of the agent identifies the agent as a compound that increases the expression of the protein.

Also disclosed are methods of identifying a compound that increases expression of a protein by: (i) providing a cell containing a reporter construct containing (a) a promoter sequence of a gene encoding QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5, and (b) a nucleotide sequence encoding a reporter protein; (ii) contacting the cell with an agent; and (iii) measuring the expression of the reporter protein in the presence of the agent, wherein an increase in the expression of the reporter protein in the presence of the agent as compared to the expression of the protein in the absence of the agent identifies the agent as a compound that increases the expression of the protein.

Also disclosed are methods of identifying a compound that increases expression of a protein by: (i) providing a cell containing a reporter construct containing (a) a promoter sequence of a gene encoding DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5, and (b) a nucleotide sequence encoding a reporter protein; (ii) contacting the cell with an agent; and (iii) measuring the expression of the reporter protein in the presence of the agent, wherein an increase in the expression of the reporter protein in the presence of the agent as compared to the expression of the protein in the absence of the agent identifies the agent as a compound that increases the expression of the protein.

Also disclosed are methods of identifying a compound that increases the activity of a protein by: (i) providing a protein selected from the group consisting of QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, and ATP13A5; (ii) contacting the protein with an agent; and (iii) measuring the activity of the protein in the presence of the agent, wherein an increase in the activity of the protein in the presence of the agent as compared to the activity of the protein in the absence of the agent identifies the agent as a compound that increases the activity the protein.

Also disclosed are methods of identifying a compound that increases the activity of a protein by: (i) providing a protein selected from the group consisting of DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, and ATP13A5; (ii) contacting the protein with an agent; and (iii) measuring the activity of the protein in the presence of the agent, wherein an increase in the activity of the protein in the presence of the agent as compared to the activity of the protein in the absence of the agent identifies the agent as a compound that increases the activity the protein.

In the foregoing methods, the agent can be a synthetic compound or a naturally occurring compound. For example, the agent can be a small molecule, nucleic acid, protein, antibody, or peptidomimetic. The cell used in the methods can be a eukaryotic cell (e.g., a yeast cell, nematode, insect, or mammalian cell), a prokaryotic cell, or a cell obtained from an alpha-synuclein transgenic animal.

Also disclosed are methods of evaluating an individual for the presence of or susceptibility to developing a synucleinopathy. The methods include the steps of: obtaining a biological sample from a first subject; analyzing the sample for the expression or activity of one or more proteins selected from the group consisting of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, and ATP13A5; and comparing the expression or activity of the one or more proteins in the sample from the first subject with the expression or activity of the one or more proteins in a sample from a second subject not having or being at risk of developing the synucleinopathy, wherein decreased expression or activity of the one or more proteins in the sample from the first subject indicates that the subject is an individual having or at risk of developing the synucleinopathy.

Also disclosed are methods of evaluating an individual for the presence of or susceptibility to developing a synucleinopathy. The methods include the steps of: obtaining a biological sample from a first subject; analyzing the sample for the expression or activity of one or more proteins selected from the group consisting of GOSR1, SEC31A, SEC31B, ADIPOR2, ADIPOR1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, and USP2; and comparing the expression or activity of the one or more proteins in the sample from the first subject with the expression or activity of the one or more proteins in a sample from a second subject not having or being at risk of developing the synucleinopathy, wherein increased expression or activity of the one or more proteins in the sample from the first subject indicates that the subject is an individual having or at risk of developing the synucleinopathy.

Also disclosed are methods of evaluating an individual for the presence of or susceptibility to developing a synucleinopathy. The methods include the steps of: obtaining a biological sample from a first subject; analyzing the sample for the expression or activity of one or more proteins selected from the group consisting of KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, and USP2; and comparing the expression or activity of the one or more proteins in the sample from the first subject with the expression or activity of the one or more proteins in a sample from a second subject not having or being at risk of developing the synucleinopathy, wherein increased expression or activity of the one or more proteins in the sample from the first subject indicates that the subject is an individual having or at risk of developing the synucleinopathy.

Also disclosed are pharmaceutical compositions containing a therapeutic or prophylactic amount of a compound that: (i) increases the expression or activity of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; or (ii) decreases the expression or activity of GOSR1, SEC31A, SEC31B, ADIPOR2, ADIPOR1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2.

Also disclosed are pharmaceutical compositions containing a therapeutic or prophylactic amount of a compound that: (i) increases the expression or activity of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5; or (ii) decreases the expression or activity of KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2.

In some embodiments, the pharmaceutical composition contains (i) a therapeutic or prophylactic amount of an isolated polypeptide selected from the group consisting of SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, and ATP13A5, and (ii) a pharmaceutically acceptable carrier.

Also disclosed are cells containing a first expression vector encoding alpha synuclein and a second expression vector encoding GOS1, SEC31, IZH3, MKS1, TPO4, GOSR1, SEC31A, SEC31B, ADIPOR2, ADIPOR1, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2. The cell can be a eukaryotic cell (e.g., a yeast cell or mammalian cell) or a prokaryotic cell.

Also disclosed are cells containing a first expression vector encoding alpha synuclein and a second expression vector encoding NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CB, PPP1CA, USP21, or USP2. The cell can be a eukaryotic cell (e.g., a yeast cell or mammalian cell) or a prokaryotic cell.

Also disclosed are cells containing a first expression vector encoding alpha synuclein and a second expression vector encoding QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5. The cell can be a eukaryotic cell (e.g., a yeast cell or mammalian cell) or a prokaryotic cell.

Also disclosed are cells containing a first expression vector encoding alpha synuclein and a second expression vector encoding DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062c, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G2, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A2 (PARK9), ATP13A1, ATP13A3, ATP13A4, or ATP13A5. The cell can be a eukaryotic cell (e.g., a yeast cell or mammalian cell) or a prokaryotic cell.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application, including definitions, will control. In addition, the materials, methods, and examples are illustrative only and not intended to be limiting.

Other features and advantages of the invention will be apparent from the following detailed description, and from the claims.

DETAILED DESCRIPTION

It has been found that overexpression of certain genes results in a modulation of alpha-synuclein mediated cellular toxicity. Compounds that modulate expression of these genes or activity of the encoded proteins can be used to inhibit alpha-synuclein mediated toxicity and used to treat or prevent synucleinopathies such as Parkinson's disease.

Modulators of Alpha-Synuclein-Mediated Toxicity

As detailed in the accompanying examples, several genes have been identified that modulate cellular toxicity associated with overexpression of alpha-synuclein in yeast cells. For those genes that were found to suppress toxicity when overexpressed in yeast, it is expected that enhancing expression of the genes and/or activity of proteins encoded by the genes will result in a suppression of toxicity in alpha-synuclein expressing cells. Conversely, for those genes that were found to enhance toxicity when overexpressed in yeast, it is expected that inhibiting expression of the genes and/or the activity of proteins encoded by the genes will result in a suppression of toxicity in alpha-synuclein expressing cells.

It is expected that the mechanisms by which alpha-synuclein induces toxicity in the yeast model system described herein is similar to the mechanisms by which alpha-synuclein induces toxicity in human cells. Many of the yeast genes identified as modulating alpha-synuclein mediated toxicity in yeast cells have orthologous or highly related genes in humans (Table 1). As a result, human counterparts of the identified yeast genes are expected to be useful targets for modulating alpha-synuclein mediated toxicity in human cells.

Table 1 lists GenBank™ Accession Numbers corresponding to the nucleotide and protein sequences for each of the human genes identified herein. As detailed in the following sections, these nucleotide and protein sequences can be used to generate compounds (including but not limited to nucleic acids, peptides, antibodies) that modulate expression of genes or activity of encoded gene products. The genes identified herein as modulators of alpha-synuclein mediated toxicity are referred to in subsequent sections (e.g., regarding screening assays) as "target genes" and the encoded proteins are referred to as "target proteins."

TABLE 1

Human Counterparts of Yeast Genes that Modulate Alpha-Synuclein Toxicity

| Yeast Gene Name | Suppressor or Enhancer | Human Gene Name | DNA Accession Number (Human) | Protein Accession Number (Human) |
|---|---|---|---|---|
| DIP5 | Suppressor | SLC7A2 | NM_003046 | NP_003037 |
| | | SLC7A13 | NM_138817 | NP_620172 |
| | | SLC7A6 | NM_001076785 | NP_001070253 |
| LST8 | Suppressor | GBL | NM_022372 | NP_071767 |
| REG1 | Suppressor | DSSP | NM_014208 | NP_055023 |
| UGP1 | Suppressor | UGP2 | NM_006759 | NP_006750 |
| SEC21 | Suppressor | COPG | NM_016128 | NP_057212 |
| | | COPG2 | NM_012133 | NP_036265 |
| SEC28 | Suppressor | COPE | NM_007263 | NP_009194 |
| SFT1 | Suppressor | BET1 | NM_005868 | NP_005859 |
| IME2 | Suppressor | ICK | NM_016513 | NP_057597 |
| | | MAK | NM_005906 | NP_005897 |
| KSP1 | Suppressor | ULK3 | AL117482 | CAB55955 |
| | | MARK2 | NM_001039469 | NP_001034558 |
| | | MARK1 | NM_018650 | NP_061120 |
| | | MARK3 | NM_002376 | NP_002367 |
| | | MARK4 | NM_031417 | NP_113605 |
| | | ULK1 | NM_003565 | NP_003556 |
| RCK2 | Suppressor | CAMK1G | NM_020439 | NP_065172 |
| | | CAMK1 | NM_003656 | NP_003647 |
| | | CAMK1D | NM_153498 | NP_705718 |
| YCK3 | Suppressor | CSNK1G3 | NM_001044723 | NP_001038188 |
| | | CSNK1G2 | NM_001319 | NP_001310 |
| | | CSNK1G1 | NM_022048 | NP_071331 |
| | | CSNK1D1 | NM_001893 | NP_001884 |
| | | CSNK1E1 | NM_152221 | NP_689407 |
| | | CSNK1A1 | NM_001025105 | NP_001020276 |
| | | CSNK1A1L | NM_145203 | NP_660204 |
| LSG1 | Suppressor | LSG1 | NM_018385 | NP_060855 |
| MGA2 | Suppressor | OSBPL1A | NM_080597 | NP_542164 |
| MUM2 | Suppressor | ERC2 | BC111550 | AAI11551 |
| OSH3 | Suppressor | OSBPL6 | NM_145739 | NP_665682 |
| | | OSBPL3 | NM_015550 | NP_056365 |
| | | OSBPL7 | NM_145798 | NP_665741 |
| | | OSBPL1A | NM_080597 | NP_542164 |
| | | OSBPL2 | NM_144498 | NP_653081 |
| PIN4 | Suppressor | CFTF2T | NM_015235 | NP_056050 |
| | | CFTF2 | NM_001325 | NP_001316 |
| URE2 | Suppressor | EEF1G | CR407625 | CAG28553 |
| PTC4 | Suppressor | PPM1G | NM_177983 | NP_817092 |
| | | PPM1A | NM_177952 | NP_808821 |
| | | PPM1B | NM_002706 | NP_002697 |
| NTH1 | Suppressor | TREH | NM_007180 | NP_009111 |
| CUP9 | Suppressor | PKNOX2 | NM_022062 | NP_071345 |
| | | PKNOX1 | NM_004571 | NP_004562 |
| JSN1 | Suppressor | PUM1 | NM_001020658 | NP_001018494 |
| | | PUM2 | NM_015317 | NP_056132 |
| TIF4632 | Suppressor | EIF4G3 | NM_003760 | NP_003751 |
| | | EIF4G1 | NM_198241 | NP_937884 |
| HRD1 | Suppressor | SYVN1 | NM_172230 | NP_757385 |
| SAN1 | Suppressor | ZNF364 | NM_014455 | NP_055270 |
| YBR030w | Suppressor | SETD6 | BC022451 | AAH22451 |
| YKL088w | Suppressor | PPCDC | NM_021823 | NP_068595 |
| YML081w | Suppressor | EGR3 | NM_004430 | NP_004421 |
| | | ZFP161 | NM_003409 | NP_003400 |
| | | EGR2 | NM_000399 | NP_000390 |
| | | HKR1 | NM_181786 | NP_861451 |
| | | ZNF740 | NM_001004304 | NP_001004304 |
| YOR291W | Suppressor | ATP13A2 (PARK9) | NM_022089 | NP_071372 |
| | | ATP13A1 | NM_020410 | NP_065143 |
| | | ATP13A3 | NM_024524 | NP_078800 |
| | | ATP13A4 | NM_032279 | NP_115655 |
| | | ATP13A5 | NM_198505 | NP_940907 |
| GOS1 | Enhancer | GOSR1 | BC012620 | AAH12620 |
| SEC31 | Enhancer | SEC31A | BC047883 | AAH47883 |
| | | SEC31B | NM_015490 | NP_056305 |
| IZH3 | Enhancer | ADIPOR2 | NM_024551 | NP_078827 |
| | | ADIPOR1 | NM_001127687 | NP_001121159 |
| NRG1 | Enhancer | KLF12 | NM_007249 | NP_009180 |
| | | KLF5 | NM_001730 | NP_001721 |

TABLE 1-continued

Human Counterparts of Yeast Genes that Modulate Alpha-Synuclein Toxicity

| Yeast Gene Name | Suppressor or Enhancer | Human Gene Name | DNA Accession Number (Human) | Protein Accession Number (Human) |
|---|---|---|---|---|
| NRG2 | Enhancer | ZNF323 | NM_145909 | NP_665916 |
| | | ZNF718 | NM_001039127 | NP_001034216 |
| | | ZNF705A | NM_001004328 | NP_001004328 |
| BET4 | Enhancer | RABGGTA | NM_004581 | NP_004572 |
| GLO3 | Enhancer | ZNF289 | NM_032389 | NP_115765 |
| SLY41 | Enhancer | SLC35E1 | NM_024881 | NP_079157 |
| TRS120 | Enhancer | NIBP | BC065288 | AAH65288 |
| YIP3 | Enhancer | RABAC1 | NM_006423 | NP_006414 |
| IDS2 | Enhancer | KIAA0999 | AB023216 | BAA76843 |
| PPZ2 | Enhancer | PPP1CC | NM_002710 | NP_002701 |
| | | PPP1CB | NM_206876 | NP_996759 |
| | | PPP1CA | NM_001008709 | NP_001008709 |
| UBP11 | Enhancer | USP21 | NM_012475 | NP_036607 |
| UBP7 | Enhancer | USP21 | NM_012475 | NP_036607 |
| | | USP2 | NM_004205 | NP_004196 |

Compounds that enhance the expression or activity of DIP5 (or human SLC7A2, SLC7A13, or SLC7A6), LST8 (or human GBL), REG1 (or human DSSP), UGP1 (or human UGP2), SEC21 (or human COPG or COPG2), SEC28 (or human COPE), SFT1 (or human BET1), IME2 (or human ICK or MAK), KSP1 (or human ULK3, MARK2, MARK1, MARK3, MARK4, or ULK1), RCK2 (or human CAMK1G, CAMK1, or CAMK1D), YCK3 (or human CSNK1G3, CSNK1G2, CSNK1G1, CSNK1D1, CSNK1E1, CSNK1A1, or CSNK1A1L), LSG1 (or human LSG1), MGA2 (or human OSBPL1A), MUM2 (or human ERC2), OSH3 (or human OSBPL6, OSBPL3, OSBPL7, OSBPL1A, or OSBPL2), PIN4 (or human CFTF2T or CFTF2), URE2 (or human EEF1G), PTC4 (or human PPM1G, PPM1A, or PPM1B), NTH1 (or human TREH), CUP9 (or human PKNOX2 or PKNOX1), JSN1 (or human PUM1 or PUM2), TIF4632 (or human EIF4G3 or EIF4G1), HRD1 (or human SYVN1), SAN1 (or human ZNF364), YBR030w (or human SETD6), YKL088w (or human PPCDC), or YOR291W (or human ATP13A2 (PARK9), ATP13A1, ATP13A3, ATP13A4, or ATP13A5) are expected to inhibit alpha-synuclein-mediated cellular toxicity. It is also understood that compounds capable of inhibiting the expression or activity of an inhibitor of DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YMR111c, YOR291W, or human counterparts of any of the foregoing are expected to inhibit alpha-synuclein-mediated cellular toxicity.

Alternatively, compounds that inhibit the expression of GOS1 (or human GOSR1), SEC31 (or human SEC31A or SEC31B), IZH3 (or human ADIPOR2 or ADIPOR1), NRG1 (or human KLF12 or KLF5), NRG2 (or human ZNF323, ZNF718, or ZNF705A), BET4 (or human RABGGTA), GLO3 (or human ZNF289), SLY41 (or human SLC35E1), TRS120 (or human NIBP), YIP3 (or human RABAC1), IDS2 (or human KIAA0999), PPZ2 (or human PPP1CC, PPP1CB, or PPP1CA), UBP11 (or human USP21), or UBP7 (or human USP21 or USP2) are expected to inhibit alpha-synuclein-mediated cellular toxicity. It is also understood that compounds capable of enhancing the expression or activity of an inhibitor of GOS1, SEC31, IZH3, NRG1, NRG2, BET4, GLO3, SLY41, TRS120, YIP3, IDS2, PPZ2, UBP11, UBP7, or human counterparts of any of the foregoing are expected to inhibit alpha-synuclein-mediated cellular toxicity.

Screening Assays

The methods described herein include methods (also referred to herein as "screening assays") for identifying compounds that modulate (i.e., increase or decrease) expression or activity of selected target genes or their protein products. Such compounds include, e.g., polypeptides, peptides, antibodies, peptidomimetics, peptoids, small inorganic molecules, small non-nucleic acid organic molecules, nucleic acids (e.g., anti-sense nucleic acids, siRNA, oligonucleotides, synthetic oligonucleotides), carbohydrates, or other agents that bind to the target proteins, have a stimulatory or inhibitory effect on, for example, expression of a target gene or activity of a target protein. Compounds thus identified can be used to modulate the expression or activity of target genes or target proteins in a therapeutic protocol.

In general, screening assays involve assaying the effect of a test agent on expression or activity of a target nucleic acid or target protein in a test sample (i.e., a sample containing the target nucleic acid or target protein). Expression or activity in the presence of the test compound or agent can be compared to expression or activity in a control sample (i.e., a sample containing the target protein that is incubated under the same conditions, but without the test compound). A change in the expression or activity of the target nucleic acid or target protein in the test sample compared to the control indicates that the test agent or compound modulates expression or activity of the target nucleic acid or target protein and is a candidate agent.

Compounds can be tested for their ability to modulate one or more activities mediated by a target protein described herein. For example, compounds that modulate expression of a gene or activity of a protein listed in Table 1 or 2 can be tested for their ability to modulate toxicity in cells expressing alpha-synuclein. Methods of assaying a compound for such activities are known in the art. In some cases, a compound is tested for it's ability to directly affect target gene expression or binding to a target protein (e.g., by decreasing the amount of target RNA in a cell or decreasing the amount of target protein in a cell) and tested for its ability to modulate a metabolic effect associated with the target protein.

In one embodiment, assays are provided for screening candidate or test molecules that are substrates of a target protein or a biologically active portion thereof in a cell. In another embodiment, the assays are for screening candidate or test compounds that bind to a target protein or modulate the activity of a target protein or a biologically active portion thereof. Such compounds include those that disrupt the interaction between a target protein and its ligand.

The test compounds used in the methods can be obtained using any of the numerous approaches in the art including combinatorial library methods, including: biological libraries; peptoid libraries (libraries of molecules having the functionalities of peptides, but with a novel, non-peptide backbone which are resistant to enzymatic degradation but which nevertheless remain bioactive; e.g., Zuckermann et al. (1994) J. Med. Chem. 37:2678); spatially addressable parallel solid phase or solution phase libraries; synthetic library methods requiring deconvolution; the "one-bead one-compound" library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the literature, for example in: DeWitt et al., Proc. Natl. Acad. Sci. USA, 90:6909, 1993; Erb et al., Proc. Natl. Acad. Sci. USA, 91:11422, 1994; Zuckermann et al., J. Med. Chem. 37:2678, 1994; Cho et al., Science 261:1303, 1993; Carrell et al., Angew. Chem. Int. Ed. Engl. 33:2059, 1994; Carell et al., Angew. Chem. Int. Ed. Engl., 33:2061, 1994; and Gallop et al., J. Med. Chem., 37:1233, 1994.

Libraries of compounds may be presented in solution (e.g., Houghten, Bio/Techniques, 13:412421, 1992), or on beads (Lam, Nature, 354:82-84, 1991), chips (Fodor, Nature 364:555-556, 1993), bacteria (U.S. Pat. No. 5,223,409), spores (U.S. Pat. Nos. 5,571,698; 5,403,484; and 5,223,409), plasmids (Cull et al., Proc. Natl. Acad. Sci. USA, 89:1865-1869, 1992) or phage (Scott and Smith, Science, 249:386-390, 1990; Devlin, Science, 249:404-406, 1990; Cwirla et al., Proc. Natl. Acad. Sci. USA, 87:6378-6382, 1990; and Felici, J. Mol. Biol., 222:301-310, 1991).

In one embodiment, a cell-based assay is employed in which a cell that expresses a target protein or biologically active portion thereof is contacted with a test compound. The ability of the test compound to modulate expression or activity of the target protein is then determined. The cell, for example, can be a yeast cell or a cell of mammalian origin, e.g., rat, mouse, or human.

The ability of the test compound to bind to a target protein or modulate target protein binding to a compound, e.g., a target protein substrate, can also be evaluated. This can be accomplished, for example, by coupling the compound, e.g., the substrate, with a radioisotope or enzymatic label such that binding of the compound, e.g., the substrate, to the target protein can be determined by detecting the labeled compound, e.g., substrate, in a complex. Alternatively, the target protein can be coupled with a radioisotope or enzymatic label to monitor the ability of a test compound to modulate target protein binding to a target protein substrate in a complex. For example, compounds (e.g., target protein substrates) can be labeled with $^{125}I$, $^{35}S$, $^{14}C$, or $^{3}H$, either directly or indirectly, and the radioisotope detected by direct counting of radioemmission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

The ability of a compound (e.g., a target protein substrate) to interact with target protein with or without the labeling of any of the interactants can be evaluated. For example, a microphysiometer can be used to detect the interaction of a compound with a target protein without the labeling of either the compound or the target protein (McConnell et al., Science 257:1906-1912, 1992). As used herein, a "microphysiometer" (e.g., Cytosensor™) is an analytical instrument that measures the rate at which a cell acidifies its environment using a light-addressable potentiometric sensor (LAPS). Changes in this acidification rate can be used as an indicator of the interaction between a compound and a target protein.

In yet another embodiment, a cell-free assay is provided in which a target protein or biologically active portion thereof is contacted with a test compound and the ability of the test compound to bind to the target protein or biologically active portion thereof is evaluated. In general, biologically active portions of target proteins to be used in assays described herein include fragments that participate in interactions with other molecules, e.g., fragments with high surface probability scores.

Cell-free assays involve preparing a reaction mixture of the target protein and the test compound under conditions and for a time sufficient to allow the two components to interact and bind, thus forming a complex that can be removed and/or detected.

The interaction between two molecules can also be detected using fluorescence energy transfer (FET) (see, for example, Lakowicz et al., U.S. Pat. No. 5,631,169; Stavrianopoulos et al., U.S. Pat. No. 4,868,103). A fluorophore label on the first, "donor" molecule is selected such that its emitted fluorescent energy will be absorbed by a fluorescent label on a second, "acceptor" molecule, which in turn is able to fluoresce due to the absorbed energy. Alternately, the "donor" protein molecule may use the natural fluorescent energy of tryptophan residues. Labels are chosen that emit different wavelengths of light, such that the "acceptor" molecule label may be differentiated from that of the "donor." Since the efficiency of energy transfer between the labels is related to the distance separating the molecules, the spatial relationship between the molecules can be assessed. In a situation in which binding occurs between the molecules, the fluorescent emission of the "acceptor" molecule label in the assay should be maximal. A FET binding event can be conveniently measured through standard fluorometric detection means well known in the art (e.g., using a fluorimeter).

In another embodiment, the ability of a target protein to bind to a target molecule can be determined using real-time Biomolecular Interaction Analysis (BIA) (e.g., Sjolander et al., Anal. Chem., 63:2338-2345, 1991, and Szabo et al., Curr. Opin. Struct. Biol., 5:699-705, 1995). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

In various of these assays, the target protein or the test substance is anchored onto a solid phase. The target protein/test compound complexes anchored on the solid phase can be detected at the end of the reaction. Generally, the target protein is anchored onto a solid surface, and the test compound (which is not anchored) can be labeled, either directly or indirectly, with detectable labels discussed herein.

It may be desirable to immobilize either the target protein, an anti-target protein antibody, or its target molecule to facilitate separation of complexed from uncomplexed forms of one or both of the proteins, as well as to accommodate automation of the assay. Binding of a test compound to a target protein, or interaction of a target protein with a target molecule in the presence and absence of a test compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, glutathione-S-transferase/target protein fusion proteins or glutathione-S-transferase/target fusion proteins can be adsorbed onto glutathione Sepharose™ beads (Sigma Chemical, St. Louis, Mo.) or glutathione derivatized microtiter plates, which are then combined with the test compound or the test compound and either the non-adsorbed target protein. The mixture is then incubated under conditions conducive to complex formation (e.g., at physiological conditions for salt and pH). Following incubation, the beads or microtiter plate wells are washed to remove any unbound components, the matrix immobilized in the case of beads, and the complex determined either directly or indirectly, for example, as described above. Alternatively, the complexes can be dissociated from the matrix, and the level of target protein binding or activity determined using standard techniques.

Other techniques for immobilizing a target protein on matrices include using conjugation of biotin and streptavidin. Biotinylated target protein can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical).

To conduct the assay, the non-immobilized component is added to the coated surface containing the anchored component. After the reaction is complete, unreacted components are removed (e.g., by washing) under conditions such that any complexes formed will remain immobilized on the solid surface. The complexes anchored on the solid surface can be detected in a number of ways. Where the previously non-immobilized component is pre-labeled, the presence of a label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

In some cases, the assay is performed utilizing antibodies reactive with target protein, but which do not interfere with binding of the target protein to its target molecule. Such antibodies can be derivatized to the wells of the plate, and unbound target protein trapped in the wells by antibody conjugation. Methods for detecting such complexes, in addition to those described above for the GST-immobilized complexes, include immunodetection of complexes using antibodies reactive with the target protein or target molecule, as well as enzyme-linked assays which rely on detecting an enzymatic activity associated with the target protein.

Alternatively, cell-free assays can be conducted in a liquid phase. In such an assay, the reaction products are separated from unreacted components, by any of a number of standard techniques, including but not limited to: differential centrifugation (see, for example, Rivas and Minton, Trends Biochem. Sci., 18:284-7, 1993); chromatography (gel filtration chromatography, ion-exchange chromatography); electrophoresis (e.g., Ausubel et al., eds. Current Protocols in Molecular Biology 1999, J. Wiley: New York.); and immunoprecipitation (see, for example, Ausubel et al., eds., 1999, Current Protocols in Molecular Biology, J. Wiley: New York). Such resins and chromatographic techniques are known to one skilled in the art (e.g., Heegaard, J. Mol. Recognit., 11: 141-148, 1998; Hage et al., J. Chromatogr. B. Biomed. Sci. Appl., 699:499-525, 1997). Further, fluorescence energy transfer may also be conveniently utilized, as described herein, to detect binding without further purification of the complex from solution.

The assay can include contacting the target protein or a biologically active portion thereof with a known compound that binds to the target protein to form an assay mixture, contacting the assay mixture with a test compound, and determining the ability of the test compound to interact with the target protein, wherein determining the ability of the test compound to interact with the target protein includes determining the ability of the test compound to preferentially bind to the target protein or biologically active portion thereof, or to modulate the activity of a target molecule, as compared to the known compound.

A target protein can, in vivo, interact with one or more cellular or extracellular macromolecules, such as proteins. For the purposes of this discussion, such cellular and extracellular macromolecules are referred to herein as "binding partners." Compounds that disrupt such interactions are useful for regulating the activity of the target protein. Such compounds can include, but are not limited, to molecules such as antibodies, peptides, and small molecules. In general, target proteins for use in identifying agents that disrupt interactions are the target proteins identified herein. In alternative embodiments, the invention provides methods for determining the ability of the test compound to modulate the activity of a target protein through modulation of the activity of a downstream effector of a target protein. For example, the activity of the effector molecule on an appropriate target can be determined, or the binding of the effector to an appropriate target can be determined, as described herein.

To identify compounds that interfere with the interaction between the target protein and its binding partner(s), a reaction mixture containing the target protein and the binding partner is prepared, under conditions and for a time sufficient, to allow the two products to form a complex. To test an inhibitory agent, the reaction mixture is provided in the presence (test sample) and absence (control sample) of the test compound. The test compound can be initially included in the reaction mixture, or can be added at a time subsequent to the addition of the target gene and its cellular or extracellular binding partner. Control reaction mixtures are incubated without the test compound or with a control compound. The formation of complexes between the target protein and the cellular or extracellular binding partner is then detected. The formation of a complex in the control reaction, and less formation of complex in the reaction mixture containing the test compound, indicates that the compound interferes with the interaction of the target protein and the interactive binding partner. Such compounds are candidate compounds for inhibiting the expression or activity or a target protein. Additionally, complex formation within reaction mixtures containing the test compound and normal target protein can also be compared to complex formation within reaction mixtures containing the test compound and mutant target gene product. This comparison can be important in those cases wherein it is desirable to identify compounds that disrupt interactions of mutant but not normal target protein.

Binding assays can be carried out in a liquid phase or in heterogenous formats. In one type of heterogeneous assay system, either the target protein or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed will remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

In another embodiment, modulators of target expression (RNA or protein) are identified. For example, a cell or cell-free mixture is contacted with a test compound and the expression of target mRNA or protein evaluated relative to the level of expression of target mRNA or protein in the absence of the test compound. When expression of target mRNA or protein is greater in the presence of the test compound than in its absence, the test compound is identified as a stimulator (candidate compound) of target mRNA or protein expression. Alternatively, when expression of target mRNA or protein is less (statistically significantly less) in the presence of the test compound than in its absence, the test compound is identified as an inhibitor (candidate compound) of target mRNA or protein expression. The level of target mRNA or protein expression can be determined by methods described herein and methods known in the art such as Northern blot or Western blot for detecting target mRNA or protein, respectively.

In another aspect, the methods described herein pertain to a combination of two or more of the assays described herein. For example, a modulating agent can be identified using a cell-based or a cell-free assay, and the ability of the agent to modulate the activity of a target protein can be confirmed in vivo, e.g., in an animal such as an animal model for Parkinson's disease.

This invention further pertains to novel agents identified by the above-described screening assays. Accordingly, it is within the scope of this invention to further use an agent (compound) identified as described herein (e.g., a target protein modulating agent, an anti sense nucleic acid molecule, an siRNA, a target protein-specific antibody, or a target protein-binding partner) in an appropriate animal model to determine the efficacy, toxicity, side effects, or mechanism of action, of treatment with such an agent. Furthermore, novel agents identified by the above-described screening assays can be used for treatments as described herein.

Compounds that modulate target protein expression or activity (target protein modulators) can be tested for their ability to affect metabolic effects associated with the target protein, e.g., with decreased expression or activity of target protein using methods known in the art and methods described herein. For example, the ability of a compound to modulate alpha-synuclein mediated toxicity can be tested using an in vitro or in vivo model for Parkinson's disease.

Target Protein Modulators

Methods of modulating target protein expression or activity can be accomplished using a variety of compounds including nucleic acid molecules that are targeted to a target nucleic acid sequence or fragment thereof, or to a target protein. Compounds that may be useful for inhibiting target protein expression or activity include polynucleotides, polypeptides, small non-nucleic acid organic molecules, small inorganic molecules, antibodies or fragments thereof, antisense oligonucleotides, siRNAs, and ribozymes. Methods of identifying such compounds are described herein.

RNA Inhibition (RNAi)

Molecules that are targeted to a target RNA are useful for the methods described herein, e.g., inhibition of target protein expression, e.g., for treating a synucleinopathy such as Parkinson's disease. Examples of nucleic acids include siRNAs. Other such molecules that function using the mechanisms associated with RNAi can also be used including chemically modified siRNAs and vector driven expression of hairpin RNA that are then cleaved to siRNA. The nucleic acid molecules or constructs that are useful as described herein include dsRNA (e.g., siRNA) molecules comprising 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is complementary to the first strand. The dsRNA molecules can be chemically synthesized, can transcribed be in vitro from a DNA template, or can be transcribed in vivo from, e.g., shRNA. The dsRNA molecules can be designed using methods known in the art, e.g., Dharmacon.com (see, siDESIGN CENTER) or "The siRNA User Guide," available on the Internet at mpibpc.gwdg.de/abteilunge-n/100/105/sirna.html.

Negative control siRNAs ("scrambled") generally have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. Controls can also be designed by introducing an appropriate number of base mismatches into the selected siRNA sequence.

The nucleic acid compositions that are useful for the methods described herein include both siRNA and crosslinked siRNA derivatives. Crosslinking can be used to alter the pharmacokinetics of the composition, for example, to increase half-life in the body. Thus, the invention includes siRNA derivatives that include siRNA having two complementary strands of nucleic acid, such that the two strands are crosslinked. For example, a 3' OH terminus of one of the strands can be modified, or the two strands can be crosslinked and modified at the 3'OH terminus. The siRNA derivative can contain a single crosslink (e.g., a psoralen crosslink). In some cases, the siRNA derivative has at its 3' terminus a biotin molecule (e.g., a photocleavable biotin), a peptide (e.g., a Tat peptide), a nanoparticle, a peptidomimetic, organic compounds (e.g., a dye such as a fluorescent dye), or dendrimer. Modifying SiRNA derivatives in this way can improve cellular uptake or enhance cellular targeting activities of the resulting siRNA derivative as compared to the corresponding siRNA, are useful for tracing the siRNA derivative in the cell, or improve the stability of the siRNA derivative compared to the corresponding siRNA.

The nucleic acid compositions described herein can be unconjugated or can be conjugated to another moiety, such as a nanoparticle, to enhance a property of the compositions, e.g., a pharmacokinetic parameter such as absorption, efficacy, bioavailability, and/or half-life. The conjugation can be accomplished using methods known in the art, e.g., using the methods of Lambert et al., Drug Deliv. Rev., 47, 99-112, 2001 (describes nucleic acids loaded to polyalkylcyanoacrylate (PACA) nanoparticles); Fattal et al., J. Control Release, 53:137-143, 1998 (describes nucleic acids bound to nanoparticles); Schwab et al., Ann. Oncol., 5 Suppl. 4:55-8, 1994 (describes nucleic acids linked to intercalating agents, hydrophobic groups, polycations or PACA nanoparticles); and Godard et al., Eur. J. Biochem., 232:404-410, 1995 (describes nucleic acids linked to nanoparticles).

The nucleic acid molecules can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion). Additionally, the molecule can be radiolabeled, e.g., using $^3$H, $^{32}$P, or other appropriate isotope.

Synthetic siRNAs can be delivered into cells by cationic liposome transfection and electroporation. Sequences that are modified to improve their stability can be used. Such modifications can be made using methods known in the art (e.g., siSTABLE™, Dharmacon). Such stabilized molecules are particularly useful for in vivo methods such as for administration to a subject to decrease target protein expression. Longer term expression can also be achieved by delivering a vector that expresses the siRNA molecule (or other nucleic acid) to a cell, e.g., a fat, liver, or muscle cell. Several methods for expressing siRNA duplexes within cells from recombinant DNA constructs allow longer-term target gene suppression in cells, including mammalian Pol III promoter systems (e.g., HI or U6/snRNA promoter systems (Tuschl, Nature Biotechnol., 20:440-448, 2002) capable of expressing functional double-stranded siRNAs; (Bagella et al., J. Cell. Physiol., 177:206-1998; Lee et al., Nature Biotechnol., 20:500-505, 2002; Paul et al., Nature Biotechnol., 20:505-508, 2002; Yu et al., Proc. Natl. Acad. Sci. USA, 99(9):6047-6052, 2002; Sui et al., Proc. Natl. Acad. Sci. USA, 99(6): 5515-5520, 2002). Transcriptional termination by RNA Pol III occurs at runs of four consecutive T residues in the DNA template, providing a mechanism to end the siRNA transcript at a specific sequence. The siRNA is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al., 1998, supra; Lee et al., 2002, supra; Paul et al., 2002, supra; Yu et al., 2002, supra; Sui et al., 2002, supra). Constructs containing siRNA sequence under the control of T7 promoter also make functional siRNAs when cotransfected into the cells with a vector expression T7 RNA polymerase (Jacque, Nature, 418:435-438, 2002).

Animal cells express a range of noncoding RNAs of approximately 22 nucleotides termed micro RNA (miRNAs) and can regulate gene expression at the post transcriptional or translational level during animal development. miRNAs are excised from an approximately 70 nucleotide precursor RNA stem-loop. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng, Mol. Cell, 9:1327-1333, 2002). When expressed by DNA vectors containing polymerase III promoters, micro-RNA designed hairpins can silence gene expression (McManus, RNA 8:842-850, 2002). Viral-mediated delivery mechanisms can also be used to induce specific silencing of targeted genes through expression of siRNA, for example, by generating recombinant adenoviruses harboring siRNA under RNA Pol II promoter transcription control (Xia et al., Nat. Biotechnol., 20(10): 1006-10, 2002).

Injection of the recombinant adenovirus vectors into transgenic mice expressing the target genes of the siRNA results in in vivo reduction of target gene expression. In an animal model, whole-embryo electroporation can efficiently deliver synthetic siRNA into post-implantation mouse embryos (Calegari et al., Proc. Natl. Acad. Sci. USA, 99:14236-14240, 2002). In adult mice, efficient delivery of siRNA can be accomplished by "high-pressure" delivery technique, a rapid injection (within 5 seconds) of a large volume of siRNA containing solution into animal via the tail vein (Liu, Gene Ther., 6:1258-1266, 1999; McCaffrey, Nature, 418:38-39, 2002; Lewis, Nature Genetics, 32:107-108, 2002). Nanoparticles and liposomes can also be used to deliver siRNA into animals. Likewise, in some embodiments, viral gene delivery, direct injection, nanoparticle particle-mediated injection, or liposome injection may be used to express siRNA in humans.

In some cases, a pool of siRNAs is used to modulate the expression of a target gene. The pool is composed of at least 2, 3, 4, 5, 8, or 10 different sequences targeted to the target gene.

SiRNAs or other compositions that inhibit target protein expression or activity are effective for ameliorating undesirable effects of a disorder related to alpha synuclein toxicity when target RNA levels are reduced by at least 25%, 50%, 75%, 90%, or 95%. In some cases, it is desired that target RNA levels be reduced by not more than 10%, 25%, 50%, or 75%. Methods of determining the level of target gene expression can be determined using methods known in the art. For example, the level of target RNA can be determined using Northern blot detection on a sample from a cell line or a subject. Levels of target protein can also be measured using, e.g., an immunoassay method.

Antisense Nucleic Acids

Antisense nucleic acids are useful for inhibiting a target protein. Such antisense nucleic acid molecules, i.e., nucleic acid molecules whose nucleotide sequence is complementary to all or part of an mRNA encoding a target protein. An antisense nucleic acid molecule can be antisense to all or part of a non-coding region of the coding strand of a nucleotide sequence encoding a target protein. The non-coding regions ("5' and 3' untranslated regions") are the 5' and 3' sequences that flank the coding region and are not translated into amino acids.

Based upon the nucleotide sequences disclosed herein, one of skill in the art can easily choose and synthesize any of a number of appropriate antisense molecules to target a gene described herein. For example, a "gene walk" comprising a series of oligonucleotides of 15-30 nucleotides spanning the length of a nucleic acid (e.g., a target nucleic acid) can be prepared, followed by testing for inhibition of expression of the gene. Optionally, gaps of 5-10 nucleotides can be left between the oligonucleotides to reduce the number of oligonucleotides synthesized and tested.

An antisense oligonucleotide can be, for example, about 5, 10, 15, 20, 25, 30, 35, 40, 45, or 50 nucleotides or more in length. An antisense nucleic acid described herein can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridin-e, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiour-acil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The new antisense nucleic acid molecules can be administered to a mammal, e.g., a human patient. Alternatively, they can be generated in situ such that they hybridize with or bind to cellular mRNA and/or genomic DNA encoding a selected polypeptide to thereby inhibit expression, e.g., by inhibiting transcription and/or translation. The hybridization can be by conventional nucleotide complementarities to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. For example, to achieve sufficient intracellular concentrations of the antisense molecules, vector constructs can be used in which the antisense nucleic acid molecule is placed under the control of a strong pol II or pol III promoter.

An antisense nucleic acid molecule can be an alpha-anomeric nucleic acid molecule. An alpha-anomeric nucleic acid molecule forms specific double-stranded hybrids with complementary RNA in which, contrary to the usual, beta-units, the strands run parallel to each other (Gaultier et al., Nucleic Acids Res., 15:6625-6641, 1987). The antisense nucleic acid molecule can also comprise a 2'-o-methylribonucleotide (Inoue et al., Nucleic Acids Res., 15:6131-6148, 1987) or a chimeric RNA-DNA analog (Inoue et al., FEBS Lett., 215:327-330, 1987).

Antisense molecules that are complementary to all or part of a target gene described herein are also useful for assaying expression of such genes using hybridization methods known in the art. For example, the antisense molecule can be labeled (e.g., with a radioactive molecule) and an excess amount of the labeled antisense molecule is hybridized to an RNA sample. Unhybridized labeled antisense molecule is removed (e.g., by washing) and the amount of hybridized antisense molecule measured. The amount of hybridized molecule is measured and used to calculate the amount of expression of the target gene. In general, antisense molecules used for this purpose can hybridize to a sequence from a target gene under high stringency conditions such as those described herein. When the RNA sample is first used to synthesize cDNA, a sense molecule can be used. It is also possible to use a double-stranded molecule in such assays as long as the double-stranded molecule is adequately denatured prior to hybridization.

Ribozymes

Ribozymes that have specificity for a target nucleic acid sequence can also be used to inhibit target gene expression. Ribozymes are catalytic RNA molecules with ribonuclease activity that are capable of cleaving a single-stranded nucleic acid, such as an mRNA, to which they have a complementary region. Thus, ribozymes (e.g., hammerhead ribozymes (described in Haselhoff and Gerlach, Nature, 334:585-591, 1988)) can be used to catalytically cleave mRNA transcripts to thereby inhibit translation of the protein encoded by the mRNA. Methods of designing and producing ribozymes are known in the art (see, e.g., Scanlon, 1999, Therapeutic Applications of Ribozymes, Humana Press). A ribozyme having specificity for a target nucleic acid molecule or fragment thereof can be designed based upon the nucleotide sequence of a target cDNA. For example, a derivative of a Tetrahymena L-19 IVS RNA can be constructed in which the nucleotide sequence of the active site is complementary to the nucleotide sequence to be cleaved in a target RNA (Cech et al. U.S. Pat. No. 4,987,071; and Cech et al., U.S. Pat. No. 5,116,742). Alternatively, an mRNA encoding a target protein or fragment thereof can be used to select a catalytic RNA having a specific ribonuclease activity from a pool of RNA molecules (See, e.g., Bartel and Szostak, Science, 261:1411-1418, 1993).

Nucleic acid molecules that form triple helical structures can also be used to modulate target protein expression. For example, expression of a target protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene, Anticancer Drug Des., 6(6):569-84, 1991; Helene, Ann. N.Y. Acad. Sci., 660:27-36, 1992; and Maher, Bioassays, 14(12):807-15, 1992.

A nucleic acid molecule for use as described herein can be modified at the base moiety, sugar moiety or phosphate backbone to improve, e.g., the stability, hybridization, or solubility of the molecule. For example, the deoxyribose phosphate backbone of a nucleic acid can be modified to generate peptide nucleic acids (see Hyrup et al., Bioorganic & Medicinal Chem., 4(1): 5-23, 1996). Peptide nucleic acids (PNAs) are nucleic acid mimics, e.g., DNA mimics, in which the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols, e.g., as described in Hyrup et al., 1996, supra; Perry-O'Keefe et al., Proc. Natl. Acad. Sci. USA, 93: 14670-675, 1996.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., 51 nucleases (Hyrup, 1996, supra; or as probes or primers for DNA sequence and hybridization (Hyrup, 1996, supra; Perry-O'Keefe et al., Proc. Natl. Acad. Sci. USA, 93: 14670-675, 1996).

PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., Nucleic Acids Res., 24:3357-63, 1996. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., Nucleic Acids Res., 17:5973-88, 1989). PNA monomers are then coupled in a stepwise manner to produce a chimeric molecule with a 5' PNA segment and a 3' DNA segment (Finn et al., Nucleic Acids Res., 24:3357-63, 1996). Alternatively, chimeric molecules can be synthesized with a 5' DNA segment and a 3' PNA segment (Peterser et al., Bioorganic Med. Chem. Lett., 5:1119-11124, 1975).

A nucleic acid targeting a target nucleic acid sequence can include appended groups such as peptides (e.g., for targeting host cell receptors in vivo), or agents facilitating transport across the cell membrane (see, e.g., Letsinger et al., Proc. Natl. Acad. Sci. USA, 86:6553-6556, 1989; Lemaitre et al., Proc. Natl. Acad. Sci. USA, 84:648-652, 1989; WO 88/09810) or the blood-brain barrier (see, e.g., WO 89/10134). In addition, oligonucleotides can be modified with hybridization-triggered cleavage agents (see, e.g., Krol et al., Bio/Techniques, 6:958-976, 1988) or intercalating agents (see, e.g., Zon, Pharm. Res., 5:539-549, 1988). To this end, the oligonucleotide may be conjugated to another molecule, e.g., a peptide, hybridization triggered cross-linking agent, transport agent, or a hybridization-triggered cleavage agent.

Polypeptides

Isolated target proteins, fragments thereof, and variants thereof are provided herein. These polypeptides can be used, e.g., as immunogens to raise antibodies, in screening methods, or in methods of treating subjects, e.g., by administration of the target proteins. An "isolated" or "purified" polypeptide or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of polypeptides in which the polypeptide of interest is separated from cellular components of the cells from which it is isolated or recombinantly produced. Thus, a polypeptide that is substantially free of cellular material includes preparations of polypeptides having less than about 30%, 20%, 10%, or 5% (by dry weight) of heterologous protein (also referred to herein as "contaminating protein"). In general, when the polypeptide or biologically active portion thereof is recombinantly produced, it is also substantially free of culture medium, i.e., culture medium represents less than about 20%, 10%, or 5% of the volume of the protein preparation. In general, when the polypeptide is produced by chemical synthesis, it is substantially free of chemical precursors or other chemicals, i.e., it is separated from chemical precursors or other chemicals that are involved in the synthesis of the polypeptide. Accordingly such preparations of the polypeptide have less than about 30%, 20%, 10%, or 5% (by dry weight) of chemical precursors or compounds other than the polypeptide of interest.

Expression of target proteins can be assayed to determine the amount of expression. Methods for assaying protein expression are known in the art and include Western blot, immunoprecipitation, and radioimmunoassay.

As used herein, a "biologically active portion" of a target protein includes a fragment of a target protein that participates in an interaction between a target proteins and a non-target protein. Biologically active portions of a target protein include peptides including amino acid sequences sufficiently homologous to the amino acid sequence of a target protein that includes fewer amino acids than a full-length target protein, and exhibits at least one activity of a target protein. Typically, biologically active portions include a domain or motif with at least one activity of the target protein. A biologically active portion of a target protein can be a polypeptide that is, for example, 10, 25, 50, 100, 200 or more amino acids in length. Biologically active portions of a target protein can be used as targets for developing agents that modulate a target protein mediated activity, e.g., compounds that inhibit target protein activity.

In some embodiments, the target protein has a sequence identical to a sequence disclosed herein (e.g., an amino acid sequence found under a GenBank™ Accession Number listed in Table 1). Other useful polypeptides are substantially identical (e.g., at least about 45%, 55%, 65%, 75%, 85%, 95%, or 99% identical) to a sequence disclosed herein (e.g., an amino acid sequence found under a GenBank™ Accession Number listed in Table 1) and (a) retains the functional activity of the target protein yet differs in amino acid sequence due to natural allelic variation or mutagenesis, or (b) exhibits an altered functional activity (e.g., as a dominant negative) where desired. Provided herein are variants that have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the polypeptide. An antagonist of a polypeptide can inhibit one or more of the activities of the naturally occurring form of the polypeptide by, for example, competitively binding to a downstream or upstream member of a cellular signaling cascade that includes the polypeptide. Thus, specific biological effects can be elicited by treatment with a variant of limited function. Treatment of a subject with a variant having a subset of the biological activities of the naturally occurring form of the polypeptide can have fewer side effects in a subject relative to treatment with the naturally occurring form of the polypeptide. In some embodiments, the variant target protein is a dominant negative form of the target protein. Dominant negatives are desired, e.g., in methods in which inhibition of target protein action is desired.

Also provided herein are chimeric or fusion proteins.

The comparison of sequences and determination of percent identity between two sequences is accomplished using a mathematical algorithm. The percent identity between two amino acid sequences is determined using the Needleman and Wunsch, J. Mol. Biol., 48:444-453, 1970) algorithm, which has been incorporated into the GAP program in the GCG software package (available on the Internet at gcg.com), using either a Blossum 62 matrix or a PAM250 matrix, and a gap weight of 16 and a length weight of 1. The percent identity between two nucleotide sequences is determined using the GAP program in the GCG software package (also available on the Internet at gcg.com), using a NWSgapdna.CMP matrix, a gap weight of 40, and a length weight of 1.

In general, percent identity between amino acid sequences referred to herein is determined using the BLAST 2.0 program, which is available to the public on the Internet at ncbi.nlm.nih.gov/BLAST. Sequence comparison is performed using an ungapped alignment and using the default parameters (Blossum 62 matrix, gap existence cost of 11, per residue gap cost of 1, and a lambda ratio of 0.85). The mathematical algorithm used in BLAST programs is described in Altschul et al., Nucleic Acids Research 25:3389-3402, 1997.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a target protein is generally replaced with another amino acid residue from the same side chain family. Alternatively, mutations can be introduced randomly along all or part of a target protein coding sequence, such as by saturation mutagenesis, and the resultant mutants can be screened for target protein biological activity to identify mutants that retain activity. The encoded protein can be expressed recombinantly and the activity of the protein can be determined.

Antibodies

A target protein, or a fragment thereof, can be used as an immunogen to generate antibodies using standard techniques for polyclonal and monoclonal antibody preparation. The full-length polypeptide or protein can be used or, alternatively, antigenic peptide fragments can be used as immunogens. The antigenic peptide of a protein comprises at least 8 (e.g., at least 10, 15, 20, or 30) amino acid residues of the amino acid sequence of a target protein, and encompasses an epitope of a target protein such that an antibody raised against the peptide forms a specific immune complex with the polypeptide.

An immunogen typically is used to prepare antibodies by immunizing a suitable subject (e.g., rabbit, goat, mouse or other mammal). An appropriate immunogenic preparation can contain, for example, a recombinantly expressed or a chemically synthesized polypeptide. The preparation can further include an adjuvant, such as Freund's complete or incomplete adjuvant, or similar immunostimulatory agent.

Polyclonal antibodies can be prepared as described above by immunizing a suitable subject with a target protein as an immunogen. The antibody titer in the immunized subject can be monitored over time by standard techniques, such as with an enzyme linked immunosorbent assay (ELISA) using immobilized polypeptide. If desired, the antibody molecules can be isolated from the mammal (e.g., from the blood) and further purified by well-known techniques, such as protein A chromatography to obtain the IgG fraction. At an appropriate time after immunization, e.g., when the specific antibody titers are highest, antibody-producing cells can be obtained from the subject and used to prepare monoclonal antibodies by standard techniques, such as the hybridoma technique originally described by Kohler and Milstein, Nature, 256: 495-497, 1975, the human B cell hybridoma technique (Kozbor et al., Immunol. Today, 4:72, 1983), the EBV-hybridoma technique (Cole et al., Monoclonal Antibodies and Cancer Therapy, Alan R. Liss, Inc., pp. 77-96, 1985) or trioma techniques. The technology for producing hybridomas is well known (see generally Current Protocols in Immunology, 30 1994, Coligan et al. (eds.) John Wiley & Sons, Inc., New York, N.Y.). Hybridoma cells producing a monoclonal antibody are detected by screening the hybridoma culture supernatants for antibodies that bind the polypeptide of interest, e.g., using a standard ELISA assay.

As an alternative to preparing monoclonal antibody-secreting hybridomas, a monoclonal antibody directed against a polypeptide can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, U.S. Pat. No. 5,223,409; WO 92/18619; WO 91/17271; WO 92/20791; WO 92/15679; WO 93/01288; WO 92/01047; WO 92/09690; WO 90/02809; Fuchs et al., Bio/Technology, 9:1370-1372, 1991; Hay et al., Hum. Antibod. Hybridomas, 3:81-85, 1992; Huse et al., Science, 246:1275-1281, 1989; Griffiths et al., EMBO J., 12:725-734, 1993.

Additionally, recombinant antibodies, such as chimeric and humanized monoclonal antibodies, including both human and non-human portions, which can be made using standard recombinant DNA techniques, are provided herein. Such chimeric and humanized monoclonal antibodies can be produced by recombinant DNA techniques known in the art, for example using methods described in WO 87/02671; European Patent Application 184,187; European Patent Application 171,496; European Patent Application 173,494; WO 86/01533; U.S. Pat. No. 4,816,567; European Patent Application 125,023; Better et al., Science, 240:1041-1043, 1988; Liu et al., Proc. Natl. Acad. Sci. USA 84:3439-3443, 1987; Liu et al., J. Immunol., 139:3521-3526, 1987; Sun et al., Proc. Natl. Acad. Sci. USA, 84:214-218, 1987; Nishimura et al., Canc. Res., 47:999-1005, 1987; Wood et al., Nature, 314:446-449, 1985; and Shaw et al., J. Natl. Cancer Inst., 80:1553-1559, 1988); Morrison, Science, 229:1202-1207, 1985; Oi et al., Bio/Techniques, 4:214, 1986; U.S. Pat. No. 5,225,539; Jones et al., Nature, 321:552-525, 1986; Verhoeyan et al., Science, 239:1534, 1988; and Beidler et al., J. Immunol., 141:4053-4060, 1988.

Completely human antibodies are particularly desirable for therapeutic treatment of human patients. Such antibodies can be produced using transgenic mice which are incapable of expressing endogenous immunoglobulin heavy and light chains genes, but which can express human heavy and light chain genes. The transgenic mice are immunized in the normal fashion with a selected antigen, e.g., all or a portion of a target protein. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, and IgE antibodies. For an overview of this technology for producing human antibodies, see Lonberg and Huszar (Int. Rev. Immunol., 13:65-93, 1995). For a detailed discussion of this technology for producing human antibodies and human monoclonal antibodies and protocols for producing such antibodies, see, e.g., U.S. Pat. No. 5,625,126; U.S. Pat. No. 5,633,425; U.S. Pat. No. 5,569,825; U.S. Pat. No. 5,661,016; and U.S. Pat. No. 5,545,806.

Completely human antibodies that recognize a selected epitope can be generated using a technique referred to as "guided selection." In this approach a selected non-human monoclonal antibody, e.g., a murine antibody, is used to guide the selection of a completely human antibody recognizing the same epitope. (Jespers et al., Biotechnology, 12:899-903, 1994).

An antibody directed against a target protein can be used to detect the polypeptide (e.g., in a cellular lysate or cell supernatant) to evaluate its abundance and pattern of expression. The antibodies can also be used diagnostically to monitor protein levels in tissue as part of a clinical testing procedure, e.g., for example, to determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Pharmaceutical Compositions

A test compound that has been screened by a method described herein and determined to modulate target protein expression or activity, can be considered a candidate compound. A candidate compound that has been screened, e.g., in an in vivo model of a synucleinopathy such as Parkinson's disease, and determined to have a desirable effect on the disorder, can be considered a candidate therapeutic agent. Candidate therapeutic agents, once screened in a clinical setting, are therapeutic agents. Candidate therapeutic agents and therapeutic agents can be optionally optimized and/or derivatized, and formulated with physiologically acceptable excipients to form pharmaceutical compositions.

The compounds described herein that can modulate target protein expression or activity can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. A parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be desirable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the methods of preparation can include vacuum drying or freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. Dosage units can also be accompanied by instructions for use.

Toxicity and therapeutic efficacy of such compounds can be determined known pharmaceutical procedures in cell cultures or experimental animals (animal models of synucleinopathies, e.g., Parkinson's disease). These procedures can be used, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the ED50 with little or no toxicity. The dosage may vary within this range depending upon the dosage form employed and the route of administration utilized. For a compound used as described herein (e.g., for treating a synucleinopathy in a subject), the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

As defined herein, a therapeutically effective amount of protein or polypeptide (i.e., an effective dosage) ranges from about 0.001 to 30 mg/kg body weight, about 0.01 to 25 mg/kg body weight, about 0.1 to 20 mg/kg body weight, about 1 to 10 mg/kg, 2 to 9 mg/kg, 3 to 8 mg/kg, 4 to 7 mg/kg, or 5 to 6 mg/kg body weight. The protein or polypeptide can be administered one time per week for between about 1 to 10 weeks, generally between 2 to 8 weeks, between about 3 to 7 weeks, or for about 4, 5, or 6 weeks. One in the art will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, or antibody can include a single treatment or can include a series of treatments.

For antibodies or a fragment thereof, the dosage is about 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration is often possible with such species-matched antibodies. Modifications such as lipidation can be used to stabilize antibodies and to enhance uptake and tissue penetration (e.g., into the brain). A method for lipidation of antibodies is described by Cruikshank et al. (J. Acquired Immune Deficiency Syndromes and Human Retrovirology, 14:193, 1997).

Compounds that modulate expression or activity of a target protein are described herein. Such a compound can be a small molecule. For example, such small molecules include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Examples of doses include milligram or microgram amounts of the small molecule per kilogram of subject or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. When one or more of these small molecules is to be administered to an animal (e.g., a human) to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

An antibody (or fragment thereof) can be conjugated to a therapeutic moiety such as a cytotoxin, a therapeutic agent, or a radioactive metal ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclophosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

A nucleic acid molecule that is useful for modulating target protein expression or activity can be inserted into a vector and the resulting vector used as gene therapy vector. Gene therapy vectors can be delivered to a subject by, for example, intravenous injection, local administration (see U.S. Pat. No. 5,328,470) or by stereotactic injection (see e.g., Chen et al. (Proc. Natl. Acad. Sci. USA, 91:3054-3057, 1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Compounds described herein and those identified as described herein can be used to treat a subject that is at risk for or has a disease associated with alpha-synuclein toxicity and/or the formation, deposition, accumulation, or persistence of synuclein fibrils, including alpha-synuclein fibrils. In certain embodiments, diseases include synucleinopathies such as Parkinson's disease (including Parkinson's disease chemically induced by exposure to environmental agents such as pesticides, insecticides, or herbicides and/or metals such as manganese, aluminum, cadmium, copper, or zinc, SNCA gene-linked Parkinson's disease, sporadic or idiopathic Parkinson's disease, or Parkin- or LRRK2-linked Parkinson's disease), dementia with Lewy bodies, pure autonomic failure, multiple system atrophy, incidental Lewy body disease, pantothenate kinase-associated neurodegeneration, Alzheimer's disease, Down's Syndrome, Gaucher disease, or the Parkinsonism-dementia complex of Guam.

Methods of identifying an individual at risk for or having a synucleinopathy are known in the art. Thus, methods and compositions for both prophylactic and therapeutic methods of treating a subject at risk of (or susceptible to) a synucleinopathy are described herein. For example, an individual who is at risk of developing Parkinson's disease (e.g., an individual whose family history includes Parkinson's disease) and/or has signs he/she will develop Parkinson's disease can be treated with the compounds and methods described herein.

As used herein, the term "treatment" is defined as the application or administration of a therapeutic compound to a patient, or application or administration of a therapeutic compound to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic compound includes, but is not limited to, small molecules such as small non-nucleic acid organic molecules, small inorganic molecules, peptides, synthetic peptides, antibodies, natural nucleic acid molecules (such as ribozymes, siRNAs, and antisense oligonucleotides), and molecules containing nucleic acid analogs.

Provided herein are methods for preventing in a subject (e.g., a human), a synucleinopathy, by administering to the subject a target protein or a compound that modulates target protein expression or at least one target protein activity. Subjects at risk for a disease that is caused or contributed to by aberrant or unwanted target protein expression or activity can be identified by, for example, any or a combination of diagnostic or prognostic assays as described herein. Administration of a prophylactic compound can occur prior to the manifestation of symptoms characteristic of full-blown disease, such that the disease or disorder is prevented or, alternatively, delayed in its progression. Methods known in the art can be used to determine the efficacy of the treatment. The appropriate compound used for treating the subject can be determined based on screening assays described herein.

It is possible that some cases of synucleinopathies are caused, at least in part, by an abnormal level of a target gene product, or by the presence of a target protein exhibiting abnormal activity. As such, the reduction in the level and/or activity of such gene products will bring about the amelioration of disorder symptoms.

As discussed, successful treatment of synucleinopathies can be brought about by techniques that serve to inhibit the expression or activity of selected target gene products. For example, compounds, e.g., an agent identified using one or more of the assays described above, that proves to exhibit negative modulatory activity, can be used as described herein to prevent and/or ameliorate symptoms of synucleinopathies. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and Fab, F(ab)$_2$ and Fab expression library fragments, scFV molecules, and epitope-binding fragments thereof).

Further, siRNA, antisense, and ribozyme molecules that inhibit expression of a target gene can also be used in accordance with the methods described herein to reduce the level of target protein expression, thus effectively reducing the level of target protein activity. Triple helix molecules can be utilized to reduce the level of target protein activity.

Another method by which nucleic acid molecules can be utilized in treating or preventing a disease that can be treated by modulating target protein expression is through the use of aptamer molecules specific for target protein. Aptamers are nucleic acid molecules having a tertiary structure that permits them to specifically bind to protein ligands (e.g., Osborne, et al., Curr. Opin. Chem. Biol., 1: 5-9, 1997; and Patel, Curr. Opin. Chem. Biol., 1:32-46, 1997). Since nucleic acid molecules may be more conveniently introduced into target cells than therapeutic protein molecules may be, aptamers offer a method by which target protein activity can be specifically decreased without the introduction of drugs or other molecules that may have pluripotent effects.

An antibody that specifically recognizes a target protein can also be used. Lipofectin™ or liposomes can be used to deliver the antibody or a fragment of the Fab region that binds to the target protein in a cell. Where fragments of the antibody are used, the smallest inhibitory fragment that binds to the target antigen is generally used. For example, peptides having an amino acid sequence corresponding to the Fv region of the antibody can be used. Alternatively, single chain neutralizing antibodies that bind to an intracellular target protein can also be administered. Such single chain antibodies can be administered, for example, by expressing nucleotide sequences encoding single-chain antibodies within the target cell population (e.g., Marasco et al., Proc. Natl. Acad. Sci. USA, 90:7889-7893, 1993).

The identified compounds that inhibit target gene expression, synthesis and/or activity can be administered to a patient at therapeutically effective doses to prevent, treat, or ameliorate synucleinopathies. A therapeutically effective dose refers to that amount of the compound sufficient to result in amelioration of symptoms of the disorders. Toxicity and therapeutic efficacy of such compounds can be determined by standard pharmaceutical procedures as described above.

The dosage of such compounds lies generally within a range of circulating concentrations that include the $ED_{50}$ with little or no toxicity. The dosage can vary within this range depending upon the dosage form employed and the route of administration utilized. For any compound used as described herein, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography.

Another example of determination of effective dose for an individual is the ability to directly assay levels of "free" and "bound" compound in the serum of the test subject. Such assays may utilize antibody mimics and/or "biosensors" that have been created through molecular imprinting techniques. The compound that is able to modulate target protein activity is used as a template, or "imprinting molecule," to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions. A detailed review of this technique can be seen in Ansell et al., Current Opinion in Biotechnology, 7:89-94, 1996 and in Shea (Trends in Polymer Science, 2:166-173, 1994). Such "imprinted" affinity matrixes are amenable to ligand-binding assays, whereby the immobilized monoclonal antibody component is replaced by an appropriately imprinted matrix. An example of the use of such matrixes in this way can be seen in Vlatakis et al. (Nature, 361:645-647, 1993). Through the use of isotope-labeling, the "free" concentration of compound that modulates the expression or activity of a target protein can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiberoptic devices, in turn allowing the dose in a test subject to be quickly optimized based on its individual $IC_{50}$. A rudimentary example of such a "biosensor" is discussed in Kriz et al., Analytical Chemistry, 67:2142-2144, 1995.

Target protein expression or activity can be modulated for therapeutic purposes. Accordingly, in some embodiments, the modulatory methods described herein involve contacting a cell with a compound that modulates one or more of the activities of a target protein associated with the cell. A compound that modulates target protein activity can be a compound as described herein, such as a nucleic acid or a protein, a naturally-occurring target molecule of a target protein (e.g., a target protein substrate or receptor), a target protein antibody, a target protein agonist or antagonist, a peptidomimetic of a target protein agonist or antagonist, or other small molecule.

In one embodiment, the compound stimulates one or more target protein activities. Examples of such stimulatory compounds include active target protein and a nucleic acid molecule encoding the target protein. In another embodiment, the compound inhibits one or more target protein activities. Examples of such inhibitory compounds include antisense target nucleic acid molecules, anti-target protein antibodies, and target protein inhibitors. These modulatory methods can be performed in vitro (e.g., by culturing cells with the compound and returning the cells to a subject) or, alternatively, in vivo (e.g., by administering the compound to a subject). As such, the new methods include treating an individual afflicted with a disease or disorder characterized by aberrant or unwanted expression or activity of a target protein or nucleic acid molecule. In one embodiment, the methods involve administering a compound (e.g., a compound identified by a screening assay described herein), or combination of compounds that modulate (e.g., up regulates or down regulates) target protein expression or activity. In another embodiment, the methods involve administering a target protein or nucleic acid molecule as therapy to compensate for reduced, aberrant, or unwanted target protein expression or activity.

Stimulation of target protein activity is desirable in situations in which target protein is abnormally downregulated and/or in which increased target protein activity is likely to have a beneficial effect. For example, stimulation of target protein activity is desirable in situations in which a target protein is downregulated and/or in which increased target protein activity is likely to have a beneficial effect. Likewise, inhibition of target protein activity is desirable in situations in which target protein is abnormally upregulated and/or in which decreased target protein activity is likely to have a beneficial effect.

In certain embodiments, one or more compounds (e.g., compounds that modulate expression or activity of different genes or proteins) can be administered, together (simultaneously) or at different times (sequentially). In addition, such compounds can be administered with another type(s) of compound(s) for treating a synucleinopathy. For example, an identified compound may be administered together with Levodopa (L-DOPA) for treating Parkinson's disease and/or therapeutic agents such as donepezil hydrochloride (Aracept), rivastigmine tartrate (Exelon), tacrine hydrochloride (Cognex), and/or galantamine hydrobromide (Reminyl).

A compound or pharmaceutical composition thereof described herein can be administered to a subject as a combination therapy with another treatment, e.g., a treatment for a synucleinopathy (see immediately above). For example, the combination therapy can include administering to the subject (e.g., a human patient) one or more additional agents that provide a therapeutic benefit to the subject who has, or is at risk of developing, (or suspected of having) a synucleinopathy such as any of those described herein. Thus, the compound or pharmaceutical composition and the one or more additional agents can be administered at the same time. Alternatively, the compound can be administered first in time and the one or more additional agents administered second in time. The one or more additional agents can be administered first in time and the compound administered second in time. The compound can replace or augment a previously or currently administered therapy. For example, upon treating with a compound of the invention, administration of the one or more additional agents can cease or diminish, e.g., be administered at lower levels. Administration of the previous therapy can also be maintained. In some instances, a previous therapy can be maintained until the level of the compound (e.g., the dosage or schedule) reaches a level sufficient to provide a therapeutic effect. The two therapies can be administered in combination.

It will be appreciated that in instances where a previous therapy is particularly toxic (e.g., a treatment for a synucleinopathy with significant side-effect profiles) or poorly tolerated by a subject (e.g., a patient), administration of a compound of the invention can be used to offset and/or lessen the amount of the previous therapy to a level sufficient to give the same or improved therapeutic benefit, but without the toxicity.

In some instances, when the subject is administered a compound or pharmaceutical composition of the invention the first therapy is halted. The subject can be monitored for a first pre-selected result, e.g., an improvement in one or more symptoms of a synucleinopathy such as any of those described herein (e.g., see above). In some cases, where the first pre-selected result is observed, treatment with the compound is decreased or halted. The subject can then be monitored for a second pre-selected result after treatment with the compound is halted, e.g., a worsening of one or more symptoms of a synucleinopathy. When the second pre-selected result is observed, administration of the compound to the subject can be reinstated or increased, or administration of the first therapy is reinstated, or the subject is administered both a compound and first therapy, or an increased amount of the compound and the first therapeutic regimen.

The compound can also be administered with a treatment for one or more symptoms (e.g., behavioral symptoms) of a synucleinopathy. For example, the compound can be co-administered (e.g., at the same time or by any combination regimen described above) with, e.g., an anti-depressant or a medication for treating insomnia, agitation, or anxiety.

Identification of Compounds that Modulate Phosphatase Activity, Geranylgeranyltransferase Activity, ATPase Activity, Ubiquitin-Specific Protease Activity, or Kinase Activity Assays for measuring phosphatase (e.g., PPZ2, PTP2, PTC4 of a homolog thereof) activity are described in, e.g., Ruiz et al. (2004) J. Biol. Chem. 279(33):34421-34430 (PPZ2); Mattison et al. (2000) Genes & Dev. 14:1229-1235 (PTP2); Keen et al. (2005) J. Biol. Chem. 280(33):29519 and Mitsuhashi et al. (2005) Mol. Cell. Biochem. 269(1-2):183. These phosphatase activity assays can be used to identify compounds that inhibit or enhance the activity of a phosphatase (e.g., PPZ2, PTP2, PTC4 or a homolog thereof) described herein. Examples of phosphatase inhibitors, include but are not limited to, okadaic acid, calculin A, tautomycin, microcystin-LR, Fostriecin, Canthardin, Thryrsiferyl-23-acetate, cyclopentaquinoline 3a,4,5,9b-tetrahydro-3H-cyclopenta[c]quinaline-4,8-dicarboxylic acid, and 3-benzoyl-naptho[1,2-b]furan-4,5-dione (McCluskey et al. (2001) Mini Rev. Med. Chem. 1:43-55; Brissen et al. (2004) Mol. Pharm. 66(4):824-833).

Assays for measuring geranylgeranyltransferase activity are described in, e.g., Farnsworth et al. (1994) Proc. Natl. Acad. Sci. USA 91(25):11963-11967 and Peterson et al. J. Biol. Chem. 281(18):12445-12450. Examples of geranylgeranyltransferase inhibitors, e.g., useful as positive controls for the assays, include imidazolyl-beta-amino acid derivatives and L-778,123 and are described in Reid et al. (2004) Biochemistry 43(28):9000-9008; Lin et al. (2004) Bioorg. Med. Chem. Lett. 14(20):5057-5062; and Saha et al. (2005) Bioorg. Med. Chem. Lett. 15(6):1713-1719. These assays can be used to identify compounds that inhibit the activity of the geranylgeranyltransferase BET4 described herein.

Assays for measuring ATPase activity are described in, e.g., Tjian et al. (1979) Proc. Natl. Acad. Sci. USA 76(2):610-614; Collins et al. (1986) Proc. Natl. Acad. Sci. USA 83:4799-4803; and Mesngon et al. (2006) J. Neurosci. 26(7): 2132-2139. Examples of geranylgeranyltransferase inhibitors, e.g., useful as positive controls for the assays, include omeprazole, geldanamycin, radicicol, cyclopiazonic acid, and lansoprazole and are described in Shinono et al. (2002) Anticancer Res. 22(5):2907-2911. These assays can be used to identify compounds that inhibit the activity of the geranylgeranyltransferase BET4 described herein.

Assays for measuring ubiquitin-specific protease activity are described in, e.g., Holowaty et al. (2003) J. Biol. Chem. 278(48):47753-47761; Ovaa et al. (2004) Proc. Natl. Acad. Sci. USA 101:2253-2258; Gilchrist et al. (2000) Biochim Biophys Acta 1481(2):297-309; Angelats et al. (2003) Mamm. Genome 14(1):31-46; and Lee et al. (2003) Reproduction, Fertility, and Development 15(2):129-133. These assays can be used to identify compounds that inhibit the activity of the ubiquitin-specific proteases described herein.

Assays for measuring kinase activity are described in, e.g., Teige et al. (2001) Proc. Natl. Acad. Sci. USA 98(10):5652-5630 (RCK2); Sedgwick et al. (2006) Biochem. J. 399(1): 151-160 (IME2); and Tipper et al. (1983) Arch. Biochem. Biophys. 227(2):386-396 (YSK3, a casein kinase I isoform). These assays can be used to, e.g., identify compounds that enhance the activity of a protein kinase such as any of those described herein.

The following are examples of the practice of the invention. They are not to be construed as limiting the scope of the invention in any way.

EXAMPLES

Example 1

Materials and Methods

Characteristics of a Less-Toxic Alpha-Synuclein Strain Used in Plasmid Overexpression Screen The two copy alpha-synuclein expressing yeast strain used for the modifier screen consisted of aSyn-YFP integrated at the HIS3 and TRP1 loci as well as a CEN-based extrachromosomal plasmid with a galactose-inducible promoter to express each putative modifier gene. The presence of the extra galactose-inducible promoter (three total) as well as the different aSyn-YFP integration sites resulted in slightly less toxicity compared to the original two copy strain (Outeiro et al. (2003) Science 302:1772). The slightly less toxic strain is referred to as ITox2C and the higher toxicity strain is referred to as HTox2C.

Growth Rates and Survivorship Assays

Growth curves were generated by growing cells overnight in synthetic media containing 2% raffinose at 30° C. to log phase and then diluting them to 0.1-0.3 $OD_{600nm}$. 2% galactose was then added and $OD_{600nm}$ readings were taken at the indicated time points. Survivorship assays were performed as described (Haynes et al. (2004) Mol Cell 15:767). Briefly, survivorship was determined by growing strains overnight in synthetic media containing raffinose to log phase followed by the addition of 2% galactose to induce expression of alpha-synuclein. To maintain wild-type cells in log phase several dilutions were made throughout the time course. At the described time points, 1 $OD_{600nm}$ was harvested, diluted 1:1000 and 300 µl of these cells were plated on synthetic media containing 2% glucose and incubated at 30° C. Colony forming units were then determined.

Alpha-Synuclein Toxicity Modifier Screen 4,954 full-length yeast ORFs were amplified by polymerase chain reaction and captured by recombination cloning into a Gateway™ pDONR221 vector (Invitrogen). The clones were sequenced from N-terminus to C-terminus and verified to be wild type. For the expression screen, the clones were transferred into a galactose-inducible expression plasmid (pBY011; CEN, URA+, ampR) using the Gateway™ technology (Invitrogen). Additional information about the Yeast FLEXGene collection is available at www.hip.harvard.edu/research/yeast_flexgene/. Plasmid DNA from the expression clones were isolated using the REAL™ miniprep kit (Qiagen). DNA was dried in individual wells of 96-well microtiter plates and transformed into a strain expressing alpha-synuclein integrated at the HIS3 and TRP1 locus. A standard lithium acetate transformation protocol was modified for automation and used by employing a BIOROBOT Rapidplate 96-well pipettor (Qiagen). The transformants were grown in synthetic deficient media lacking uracil (SD-Ura) with glucose overnight. The overnight cultures were inoculated into fresh SD-Ura media with raffinose and allowed to reach stationary phase. The cells were spotted on to SD-Ura+glucose and SD-Ura+galactose agar plates. Suppressors of alpha-synuclein induced toxicity were identified on galactose plates after 2-3 days of growth at 30° C. The screens were repeated three independent times and candidate modifier genes were retested at least twice to confirm their authenticity. To exclude the possibility of false positive toxicity suppressor genes caused by a simple reduction in alpha-synuclein expression, the amount of alpha-synuclein protein was monitored by western blotting and flow cytometry. To exclude false-positive enhancer genes caused by a general inhibition of growth unrelated to alpha-synuclein expression, these genes were transformed into wild type yeast cells and their effect on growth determined.

Example 2

Plasmid Overexpression Screen Identifies Modifiers of Alpha-Synuclein Toxicity A genetic approach was employed to identify critical lethal lesions. An over-expression library was used in which individual yeast open reading frames were fully sequenced and placed without protein tags under the control of a galactose-inducible promoter. The 4,954 randomly selected genes in this library, representing all functional classes, were individually transformed into a yeast strain expressing aSyn-WT. A yeast strain was used that exhibited a slightly lower level of alpha-synuclein expression than described previously (Outeiro et al. (2003) Science 302:1772 and Example 1). The extended time course for toxicity produced some growth on galactose-containing agar plates, allowing for screening simultaneously for enhancers and suppressors of toxicity. Genes were identified that either suppressed or enhanced alpha-synuclein toxicity when overexpressed (Table 2). One functional class enriched in the screen provided proof-of-principle for the effectiveness of the screen. These genes were either involved in carbohydrate metabolism and galactose-regulated gene expression specifically, or produced a more general inhibition of gene expression.

TABLE 2

Yeast Genes that Modulate Alpha-Synuclein Toxicity When Overexpressed

| Type of Gene | Gene Name (SGD Gene ID) | Suppressor or Enhancer | Potential Function |
|---|---|---|---|
| Amino Acid Transport | DIP5 (YPL265W) | Suppressor | Dicarboxylic amino acid permease, mediates high-affinity and high-capacity transport of L-glutamate and L-aspartate; also a transporter for Gln, Asn, Ser, Ala, and Gly. |
| Carbohydrate Metabolism | MIG1 (YGL035C) | Suppressor | Transcription factor involved in glucose repression; C2H2 zinc finger protein similar to mammalian Egr and Wilms tumor proteins. |
| | MIG3 (YER028C) | Suppressor | Probable transcriptional repressor involved in response to toxic agents such as hydroxyurea that inhibit |

TABLE 2-continued

Yeast Genes that Modulate Alpha-Synuclein Toxicity When Overexpressed

| Type of Gene | Gene Name (SGD Gene ID) | Suppressor or Enhancer | Potential Function |
|---|---|---|---|
| | | | ribonucleotide reductase; phosphorylation by Snf1p or the Mec1p pathway inactivates Mig3p, allowing induction of damage response genes. |
| | YOR062C (YOR062C) | Suppressor | Protein of unknown function; similar to YKR075Cp and Reg1p; expression regulated by glucose and Rgt1p. |
| | UGP1 (YKL035W) | Suppressor | UDP-glucose pyrophosphorylase (UGPase), catalyses the reversible formation of UDP-Glc from glucose 1-phosphate and UTP, involved in a wide variety of metabolic pathways, expression modulated by Pho85p through Pho4p. |
| | REG1 (YDR028C) | Suppressor | Regulatory subunit of type 1 protein phosphatase Glc7p, involved in Negative regulation of glucose-repressible genes. |
| | MIG2 (YGL209W) | Suppressor | Protein containing zinc fingers, involved in repression, along with Mig1p, of SUC2 (invertase) expression by high levels of glucose; binds to Mig1p-binding sites in SUC2 promoter. |
| | GIS3 (YLR094C) | Suppressor | Protein of unknown function. multicopy suppressor of the Gal-phenotype of snf1 mig1 srb8/10/11 cells |
| | SIP5 (YMR140W) | Enhancer | Protein of unknown function; interacts with both the Reg1p/Glc7p phosphatase and the Snf1p kinase. |
| | NRG2 (YBR066C) | Enhancer | Transcriptional repressor that mediates glucose repression and negatively regulates filamentous growth; has similarity to Nrg1p. |
| | NRG1 (YDR043C) | Enhancer | Transcriptional repressor that recruits the Cyc8p-Tup1p complex to promoters; mediates glucose repression and negatively regulates a variety of processes including filamentous growth and alkaline pH response. |
| ER To Golgi Transport | SEC21 (YNL287W) | Suppressor | Gamma subunit of coatomer, a heptameric protein complex that together with Arf1p forms the COPI coat; involved in ER to Golgi transport of selective cargo. |
| | SEC28 (YIL076W) | Suppressor | Epsilon-COP subunit of the coatomer; regulates retrograde Golgi-to-ER protein traffic; stabilizes Cop1p, the alpha-COP and the coatomer complex; non-essential for cell growth. |
| | SFT1 (YKL006C-A) | Suppressor | Intra-Golgi v-SNARE, required for transport of proteins between an early and a later Golgi compartment. |
| | GLO3 (YER122C) | Enhancer | ADP-ribosylation factor GTPase activating protein (ARF GAP), involved in ER-Golgi transport; shares functional similarity with Gcs1p. |
| | TRS120 (YDR407C) | Enhancer | One of 10 subunits of the transport protein particle (TRAPP) complex of the cis-Golgi which mediates vesicle docking and fusion; involved in endoplasmic reticulum (ER) to Golgi membrane traffic. |
| | YIP3 (YNL044W) | Enhancer | Protein localized to COPII vesicles, proposed to be involved in ER to Golgi transport; interacts with |

TABLE 2-continued

Yeast Genes that Modulate Alpha-Synuclein Toxicity When Overexpressed

| Type of Gene | Gene Name (SGD Gene ID) | Suppressor or Enhancer | Potential Function |
|---|---|---|---|
| | | | members of the Rab GTPase family and Yip1p. |
| | BET4 (YJL031C) | Enhancer | Alpha subunit of Type II geranylgeranyltransferase required for vesicular transport between the endoplasmic reticulum and the Golgi; provides a membrane attachment moiety to Rab-like proteins Ypt1p and Sec4p. |
| | SLY41 (YOR307C) | Enhancer | Protein involved in ER-to-Golgi transport. |
| | GOS1 (YHL031C) | Enhancer | v-SNARE protein involved in Golgi transport, homolog of the mammalian protein GOS-28/GS28 |
| | SEC31 (YDL195W) | Enhancer | Essential phosphoprotein component (p150) of the COPII coat of secretory pathway vesicles, in complex with Sec13p; required for ER |
| Kinase | RCK2 (YLR248W) | Suppressor | Protein kinase involved in the response to oxidative and osmotic stress; identified as suppressor of S. pombe cell cycle checkpoint mutations. |
| | IME2 (YJL106W) | Suppressor | Serine/threonine protein kinase involved in activation of meiosis, associates with Ime1p and mediates its stability, activates Ndt80p; IME2 expression is positively regulated by Ime1p. |
| | YCK3 (YER123W) | Suppressor | Palmitoylated, vacuolar membrane-localized casein kinase I isoform; negatively regulates vacuole fusion during hypertonic stress via phosphorylation of the HOPS complex subunit, Vps41p; shares overlapping essential functions with Hrr25p. |
| | KSP1 (YHR082C) | Suppressor | Nonessential putative serine/threonine protein kinase of unknown cellular role; overproduction causes allele-specific suppression of the prp20-10 mutation. |
| Phosphatase | PTP2 (YOR208W) | Suppressor | Phosphotyrosine-specific protein phosphatase involved in the inactivation of mitogen-activated protein kinase (MAPK) during osmolarity sensing; dephosporylates Hog1p MAPK and regulates its localization; localized to the nucleus. |
| | PTC4 (YBR125C) | Suppressor | Cytoplasmic type 2C protein phosphatase; identified as a high-copy number suppressor of the synthetic lethality of a cnb1 mpk1 double deletion; overexpression decreases high-osmolarity induced Hog1p phosphorylation and kinase activity. |
| | PPZ2 (YDR436W) | Enhancer | Serine/threonine protein phosphatase Z, isoform of Ppz1p; involved in regulation of potassium transport, which affects osmotic stability, cell cycle progression, and halotolerance. |
| TOR Pathway | LST8 (YNL006W) | Suppressor | Protein required for the transport of amino acid permease Gap1p from the Golgi to the cell surface; component of the TOR signaling pathway; associates with both Tor1p and Tor2p; contains a WD-repeat. |

TABLE 2-continued

Yeast Genes that Modulate Alpha-Synuclein Toxicity When Overexpressed

| Type of Gene | Gene Name (SGD Gene ID) | Suppressor or Enhancer | Potential Function |
|---|---|---|---|
| Transcription/ Translation | ZDS2 (YML109W) | Suppressor | Protein that interacts with silencing proteins at the telomere, involved in transcriptional silencing; paralog of Zds1p. |
| | ZDS1 (YMR273C) | Suppressor | Protein that interacts with silencing proteins at the telomere, involved in transcriptional silencing; has a role in localization of Bcy1p, a regulatory subunit of protein kinase A; implicated in mRNA nuclear export. |
| | SKO1 (YNL167C) | Suppressor | Basic leucine zipper (bZIP) transcription factor of the ATF/CREB family that forms a complex with Tup1p and Ssn6p to both activate and repress transcription; cytosolic and nuclear protein involved in the osmotic and oxidative stress responses. |
| | HAP4 (YKL109W) | Suppressor | Subunit of the heme-activated, glucose-repressed Hap2p/3p/4p/5p CCAAT-binding complex, a Transcriptional activator and global regulator of respiratory gene expression; provides the principal activation function of the complex. |
| | VHR1 (YIL056W) | Suppressor | Transcription factor |
| | TIF4632 (YGL049C) | Suppressor | Translation initiation factor eIF4G, subunit of the mRNA cap-binding protein complex (eIF4F) that also contains eIF4E (Cdc33p); associates with the poly(A)-binding protein Pab1p, also interacts with eIF4A (Tif1p); homologous to Tif4631p. |
| | SUM1 (YDR310C) | Suppressor | Transcriptional repressor required for repression of middle sporulation-specific genes during mitosis; regulated by the pachytene checkpoint; a dominant mutation acts as a suppressor of silencing defects of SIR2 mutations. |
| | STB3 (YDR169C) | Suppressor | Protein that binds Sin3p in a two-hybrid assay. |
| | CUP9 (YPL177C) | Suppressor | Homeodomain-containing transcriptional repressor of PTR2, which encodes a major peptide transporter; imported peptides activate ubiquitin-dependent proteolysis, resulting in degradation of Cup9p and de-repression of PTR2 transcription. |
| | JSN1 (YJR091C) | Suppressor | Member of the Puf family of RNA-binding proteins, interacts with mRNAs encoding membrane-associated proteins; overexpression suppresses a tub2-150 mutation and causes increased sensitivity to benomyl in wild-type cells. |
| | MATALPHA1 (YCR040W) | Enhancer | Transcriptional co-activator involved in regulation of mating-type-specific gene expression; targets the transcription factor Mcm1p to the promoters of alpha-specific genes; one of two genes encoded by the MATalpha mating type cassette. |
| | MKS1 (YNL076W) | Enhancer | Pleiotropic negative transcriptional regulator involved in Ras-CAMP and lysine biosynthetic pathways and nitrogen regulation; involved in retrograde (RTG) mitochondria-to-nucleus signaling |

TABLE 2-continued

Yeast Genes that Modulate Alpha-Synuclein Toxicity When Overexpressed

| Type of Gene | Gene Name (SGD Gene ID) | Suppressor or Enhancer | Potential Function |
|---|---|---|---|
| Trehalose | NTH1 (YDR001C) | Suppressor | Neutral trehalase, degrades trehalose; required for thermotolerance and may mediate resistance to other cellular stresses; may be phosphorylated by Cdc28p. |
| Ubiquitination | HRD1 (YOL013C) | Suppressor | Ubiquitin-protein ligase required for endoplasmic reticulum-associated degradation (ERAD) of misfolded proteins; genetically linked to the unfolded protein response (UPR); regulated through association with Hrd3p; contains an H2 ring finger. |
| | SAN1 (YDR143C) | Suppressor | Ubiquitin-protein ligase, controls turnover of a specific class of unstable nuclear proteins including Sir4p but not Sir2p or Sir3p; san1 mutations suppress sir4, spt16, and cdc68 mutations, suggesting a role in chromatin silencing. |
| | UBP7 (YIL156W) | Enhancer | Ubiquitin-specific protease that cleaves ubiquitin-protein fusions. |
| | UBP11 (YKR098C) | Enhancer | Ubiquitin-specific protease that cleaves ubiquitin from ubiquitinated proteins. |
| Other | PFS1 (YHR185C) | Suppressor | Sporulation protein required for prospore membrane formation at selected spindle poles, ensures functionality of all four spindle pole bodies of a cell during meiosis II; not required for meiotic recombination or meiotic chromosome segregation. |
| | MUM2 (YBR057C) | Suppressor | Cytoplasmic protein essential for meiotic DNA replication and sporulation; interacts with Orc2p, which is a component of the origin recognition complex. |
| | OSH3 (YHR073W) | Suppressor | Member of an oxysterol-binding protein family with seven members in S. cerevisiae; family members have overlapping, redundant functions in sterol metabolism and collectively perform a function essential for viability. |
| | PIN4 (YBL051C) | Suppressor | Protein involved in G2/M phase progression and response to DNA damage, interacts with Rad53p; contains an RNA recognition motif, a nuclear localization signal, and several SQ/TQ cluster domains; hyperphosphorylated in response to DNA damage. |
| | MGA2 (YIR033W) | Suppressor | ER membrane protein involved, with its homolog Spt23p, in regulation of OLE1 transcription; inactive ER form dimerizes and one subunit is then activated by ubiquitin/proteasome-dependent processing followed by nuclear targeting. |
| | OSH2 (YDL019C) | Suppressor | Member of an oxysterol-binding protein family with seven members in S. cerevisiae; family members have overlapping, redundant functions in sterol metabolism and collectively perform a function essential for viability. |
| | URE2 (YNL229C) | Suppressor | Nitrogen catabolite repression regulator that acts by inhibition of GLN3 transcription in good nitrogen source; altered form of Ure2p creates [URE3] prion. |

TABLE 2-continued

Yeast Genes that Modulate Alpha-Synuclein Toxicity
When Overexpressed

| Type of Gene | Gene Name (SGD Gene ID) | Suppressor or Enhancer | Potential Function |
|---|---|---|---|
| | ISN1 (YOR155C) | Suppressor | Inosine 5'-monophosphate (IMP)-specific 5'-nucleotidase, catalyzes the breakdown of IMP to inosine, does not show similarity to known 5'-nucleotidases from other organisms. |
| | LSG1 (YGL099W) | Suppressor | Putative GTPase involved in 60S ribosomal subunit biogenesis; required for the release of Nmd3p from 60S subunits in the cytoplasm. |
| | IDS2 (YJL146W) | Enhancer | Protein involved in modulation of Ime2p activity during meiosis, appears to act indirectly to promote Ime2p-mediated late meiotic functions; found in growing cells and degraded during sporulation. |
| | IZH3 (YLR023C) | Enhancer | Membrane protein involved in zinc metabolism, member of the four-protein IZH family, expression induced by zinc deficiency; deletion reduces sensitivity to elevated zinc and shortens lag phase, overexpression reduces Zap1p activity |
| | QDR3 (YBR043C) | Suppressor | Multidrug transporter of the major facilitator superfamily, required for resistance to quinidine, barban, cisplatin, and bleomycin |
| | TPO4 (YOR273C) | Enhancer | Polyamine transport protein, recognizes spermine, putrescine, and spermidine; localizes to the plasma membrane; member of the major facilitator superfamily |
| Unknown | | | |
| | YKL088W (YKL088W) | Suppressor | Protein required for cell viability. Predicted phosphopantothenoylcysteine decarboxylase, may be involved in coenzyme A biosynthesis; interacts with Sis2p and Vhs3p |
| | YOR291W (YOR291W) | Suppressor | Probable cation-transporting ATPase 2 |
| | YML081W (YML081W) | Suppressor | Hypothetical protein. |
| | YBR030W (YBR030W) | Suppressor | Hypothetical protein. |
| | YMR111C (YMR111C) | Suppressor | Hypothetical protein. green fluorescent protein (GFP)-fusion protein localizes to the nucleus |

SGD stands for *Saccharomyces* Genome Database, which is available at yeastgenome.org and/or ensembl.org/Saccharomyces_cerevisiae.

OTHER EMBODIMENTS

It is to be understood that, while the invention has been described in conjunction with the detailed description thereof, the foregoing description is intended to illustrate and not limit the scope of the invention. Other aspects, advantages, and modifications of the invention are within the scope of the claims set forth below.

What is claimed is:

1. A cell comprising a first expression vector encoding alpha synuclein and a second expression vector encoding GOS1, SEC31, GOSR1, SEC31A, SEC31B, ADIPOR2, ADIPOR1, IZH3, MKS1, TPO4, NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CA, USP21, or USP2.

2. The cell of claim 1, wherein the second expression vector encodes NRG1, NRG2, BET4, GLO3, SLY41, TRS120, YIP3, IDS2, PPZ2, UBP11, UBP7, SIP5, MATALPHA1, KLF12, KLF5, ZNF323, ZNF718, ZNF705A, RABGGTA, ZNF289, SLC35E1, NIBP, RABAC1, KIAA0999, PPP1CC, PPP1CA, USP21, or USP2.

3. A cell comprising a first expression vector encoding alpha synuclein and a second expression vector encoding QDR3, DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062C, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, EIF4G3, EIF4G1, SYVN1, ZNF364, SETD6, PPCDC, EGR3, ZFP161, EGR2, HKR1, ZNF740, ATP13A1, ATP13A3, ATP13A4, or ATP13A5.

4. The cell of claim 3, wherein the second expression vector encodes DIP5, LST8, REG1, UGP1, SEC21, SEC28, SFT1, IME2, KSP1, RCK2, YCK3, LSG1, MGA2, MUM2, OSH3, PIN4, URE2, PTC4, NTH1, CUP9, JSN1, TIF4632, HRD1, SAN1, YBR030w, YKL088w, YML081w, YMR111c, YOR291W, YOR062C, GIS3, PTP2, SKO1, HAP4, VHR1, SUM1, STB3, PFS1, OSH2, ISN1, SLC7A2, SLC7A13, SLC7A6, GBL, DSSP, UGP2, COPG, COPG2, COPE, BET1, ICK, MAK, ULK3, MARK2, MARK1, MARK3, MARK4, ULK1, CAMK1G, CAMK1, CAMK1D, CSNK1G3, CSNK1G1, CSNK1D1, CSNK1E1, CSNK1A1, CSNK1A1L, LSG1, OSBPL1A, ERC2, OSBPL6, OSBPL3, OSBPL7, OSBPL1A, OSBPL2, CFTF2T, CFTF2, EEF1G, PPM1G, PPM1A, PPM1B, TREH, PKNOX2, PKNOX1, PUM1, PUM2, EIF4G3, EIF4G1, SYVN1, ZNF364, SETD6, PPCDC, EGR3, ZFP161, EGR2, HKR1, ZNF740, ATP13A1, ATP13A3, ATP13A4, or ATP13A5.

5. The cell of claim 1, wherein the cell is a yeast cell.
6. The cell of claim 1, wherein the cell is a mammalian cell.
7. The cell of claim 3, wherein the cell is a yeast cell.
8. The cell of claim 3, wherein the cell is a mammalian cell.

* * * * *

UNITED STATES PATENT AND TRADEMARK OFFICE
CERTIFICATE OF CORRECTION

| | | |
|---|---|---|
| PATENT NO. | : 9,249,444 B2 | Page 1 of 1 |
| APPLICATION NO. | : 13/931004 | |
| DATED | : February 2, 2016 | |
| INVENTOR(S) | : Susan L. Lindquist and Aaron D. Gitler | |

It is certified that error appears in the above-identified patent and that said Letters Patent is hereby corrected as shown below:

In the claims,

Column 55, Claim 4

Line 24, delete "PUM2,".

Signed and Sealed this
Tenth Day of May, 2016

Michelle K. Lee
*Director of the United States Patent and Trademark Office*